(12) United States Patent
Hansson et al.

(10) Patent No.: US 8,389,468 B2
(45) Date of Patent: *Mar. 5, 2013

(54) APPROACH TO THE TREATMENT OF COMPARTMENT SYNDROME

(75) Inventors: Hans-Arne Hansson, Hovås (SE); Stefan Lange, Göteborg (SE); Eva Jennische, Göteborg (SE); Tomas Bergström, Göteborg (SE)

(73) Assignee: Lantmannen AS-Faktor AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/025,702

(22) Filed: Feb. 11, 2011

(65) Prior Publication Data

US 2011/0305773 A1    Dec. 15, 2011

Related U.S. Application Data

(60) Division of application No. 12/289,389, filed on Oct. 27, 2008, now Pat. No. 8,309,513, which is a continuation of application No. PCT/SE2007/000413, filed on Apr. 27, 2007.

(30) Foreign Application Priority Data

Apr. 27, 2006 (SE) ...................................... 0600933

(51) Int. Cl.
*A61K 38/16* (2006.01)
*A61K 38/08* (2006.01)
*A61K 38/00* (2006.01)

(52) U.S. Cl. ......... 514/2; 514/21.2; 514/21.4; 514/21.7; 530/300; 530/350; 530/21.9

(58) Field of Classification Search ........................ None
See application file for complete search history.

(56) References Cited

U.S. PATENT DOCUMENTS

| 6,344,440 B1* | 2/2002 | Lonnroth et al. ............... 514/5.5 |
| 2003/0143284 A1* | 7/2003 | Lange et al. .................. 424/581 |
| 2004/0221431 A1 | 11/2004 | Wittmann |
| 2010/0227817 A1 | 9/2010 | Walsh et al. |

FOREIGN PATENT DOCUMENTS

| WO | WO 95/08992 A1 | 4/1995 |
| WO | WO 96/17602 A1 | 6/1996 |
| WO | WO 97/08202 A1 | 3/1997 |
| WO | WO 98/21978 A1 | 5/1998 |
| WO | WO 00/38535 A1 | 7/2000 |
| WO | WO 2005/030246 A1 | 4/2005 |
| WO | WO 2007/126363 A2 | 11/2007 |
| WO | WO 2007/126365 A2 | 11/2007 |

OTHER PUBLICATIONS

Wikipedia (2010) "Compartment Syndrome", http://en.wikipedia.org/wiki/Compartment_syndrome, pp. 1-4.*
Castro et al. (2000) Orbital compartment syndrome caused by intraorbital bacitracin ointment after endoscopic sinus surgery, Am. J. Ophthalmol., vol. 130, issue 3, pp. 376-378.*
Lima et al. (2009) Orbital Compartment Syndrome: The Ophthalmic Surgical Emergency, Survey Ophthalmol., vol. 54, pp. 441-449.*
Ortho-preferred (2011, updated) compartment Syndrome, http://www.wheelessonline.com/ortho/ compartment_syndrome, pp. 1-3.*
Causes of Compartment syndrome (2011, updated) www.wrongdiagnosis.com/symptoms/ compartment_syndrome /causes.htm, pp. 1-5.*
Lippincott's Nursing center.com (2011, updated) http://www.nursingcenter. com/prodev/ce_article.asp?tid=855245, pp. 1-4.*
O'Toole et al. (2009) Variation in diagnosis of compartment syndrome by surgeons treating tibial shaft fractures, J. Trauma, vol. 67, No. 4, pp. 735-741.*
Attachment 1 (2011) pp. 1-2; and attachment 2 (2011) pp. 1-2.*
Philips et al. (2002) History of head trauma and risk of intracranial meningioma: population-based case-control study, Neurology, vol. 58, No. 12, pp. 1849-1852.*
"Causes of Compartment syndrome" (2012, updated) www.wrongdiagnosis.com/ symptoms/ compartment_syndrome/causes.htm, pp. 1-5.*
Adrenal Gland Cancer: Integrative Cancer Treatment Program (2012, updated) www.cancercenter.com/adrenal_cancer.cfm, pp. 1-3.*
Oester et al. (2012) Radiographic Predictors of Visual Outcome in Orbital Compartment Syndrome, (Abstract only), Ophthalmic Plastic & Reconstructive Surgery, vol. 28, No. 1, pp. 7-10.*
Tyler et al. (2007 Long-term colonic hypersensitivity in adult rats induced by neonatal unpredictable vs predictable shock, Neurogastroenterol Motil., vol. 19, No. 19, pp. 761-768.*
Rajendran, Lawrence et al; *Raft Association and Lipid Droplet Targeting of Flotillins Are Independent of Caveolin*; Biol. Chem., vol. 388, pp. 307-314; Mar. 2007.
Alvarado, J.A. et al; *A New Insight Into the Cellular Regulation of Aqueous Outflow*; www.bjophthalmol.com, Dec. 13, 2007, XP-002462343, pp. 1500-1505.
Freeman, Michael R. et al; *Transit of Hormonal and EGF Receptor-Dependent Signals Through Cholesterol-Rich Membranes*; www.elsevier.com, Steroids 72 (2007) pp. 210-217.
Márquez, Diana C., et al; *Estrogen Receptors in Membrane Lipid Rafts and Signal Transduction in Breast Cancer*; Molecular and Cellular Endocrinology 246 (2006) pp. 91-100.
Helms, J. Bernd and Zurzolo, Chiara; *Lipids as Targeting Signals: Lipid Rafts and Intracellular Trafficking*; Traffic 2004, vol. 5, Blackwell Munksgaard, pp. 247-254.
Chini, B and Parenti, M; *G-Protein Coupled Receptors in Lipid Rafts and Caveolae: How, When and Why Do They Go There?*; Journal of Molecular Endocrinology (2004) 32, pp. 325-338.
Triantafilou, Kathy and Triantafilou, Martha; *Lipid-Raft-Dependent Coxsackievirus B4 Internalization and Rapid Targeting to the Golgi*; Virology 326 (2004) pp. 6-19.

(Continued)

*Primary Examiner* — Manjunath Rao
*Assistant Examiner* — Samuel Liu
(74) *Attorney, Agent, or Firm* — Womble Carlyle Sandridge & Rice LLP

(57) ABSTRACT

The present invention relates to the use of an antisecretory protein or a derivative, homologue, and/or fragment thereof, having antisecretory activity, and/or a pharmaceutically active salt thereof, for the manufacture of a pharmaceutical composition and/or a medical food for the treatment and/or prevention of compartment syndrome. A compartment syndrome may be caused by or a cause of a variety of other conditions which are also encompassed by the present invention, such as viral and bacterial infections. Furthermore, the invention relates to a method for the treatment and/or prevention of compartment syndrome in a mammal in need thereof.

20 Claims, 11 Drawing Sheets

OTHER PUBLICATIONS

Pohl, Jürgen et al; Long-Chain Fatty Acid Uptake Unto Adipocytes Depends on Lipid Raft Function; *Biochemistry* 2004, 43, pp. 4179-4187.

Lange, Stefan and Lönnroth, Ivar; *The Antisecretory Factor: Synthesis, Anatomical and Cellular Distribution, and Biological Action in Experimental and Clinical Studies*; International Review of Cytology, vol. 210, pp. 39-75, (2001).

Dermine, Jean-François et al; *Flotillin-1-Enriched Lipid Raft Domains Accumulate on Maturing Phagosomes*; The Journal of Biological Chemistry, vol. 276, No. 21, May 25, 2001, pp. 18507-18512.

Kurzchalia, Teymuras V. and Parton, Robert G.; *Membrane Microdomains and Caveolae*; Current Opinion in Cell Biology, 1999, pp. 424-431.

Figaji et al. (2006) Surgical treatment of 'brain compartment syndrome' in children with severe head injury, S. Afr. Med., vol. 96, pp. 969-975.

WebMD (2011, undated) "Brain swelling", www.webmd.com/brain/brain-swelling-brain-edema-intracranial-pressure, pp. 1-2.

SEQ alignment 1 (2011) pp. 1-3.

WebMD (2010, undated) "Brain & Nervous System health center", http://www.webmd.com/brain/brain-swelling-brain-edema-intracranial-pressure, pp. 1-2.

Merck (2010, undated) "Compartment syndrome", www.merck.com/mmpe/sec21/ch309/ch309c.html, pp. 1-2.

* cited by examiner

```
Met Val Leu Glu Ser Thr Met Val Cys Val Asp Asn Ser Glu Tyr Met
1               5                   10                  15
Arg Asn Gly Asp Phe Leu Pro Thr Arg Leu Gln Ala Gln Gln Asp Ala
            20                  25                  30
Val Asn Ile Val Cys His Ser Lys Thr Arg Ser Asn Pro Glu Asn Asn
            35                  40                  45
Val Gly Leu Ile Thr Leu Ala Asn Asp Cys Glu Val Leu Thr Thr Leu
            50                  55                  60
Thr Pro Asp Thr Gly Arg Ile Leu Ser Lys Leu His Thr Val Gln Pro
65                  70                  75                  80
Lys Gly Lys Ile Thr Phe Cys Thr Gly Ile Arg Val Ala His Leu Ala
            85                  90                  95
Leu Lys His Arg Gln Gly Lys Asn His Lys Met Arg Ile Ile Ala Phe
            100                 105                 110
Val Gly Ser Pro Val Glu Asp Asn Glu Lys Asp Leu Val Lys Leu Ala
            115                 120                 125
Lys Arg Leu Lys Lys Glu Lys Val Asn Val Asp Ile Ile Asn Phe Gly
        130                 135                 140
Glu Glu Glu Val Asn Thr Glu Lys Leu Thr Ala Phe Val Asn Thr Leu
145                 150                 155                 160
Asn Gly Lys Asp Gly Thr Gly Ser His Leu Val Thr Val Pro Pro Gly
            165                 170                 175
Pro Ser Leu Ala Asp Ala Leu Ile Ser Ser Pro Ile Leu Ala Gly Glu
            180                 185                 190
Gly Gly Ala Met Leu Gly Leu Gly Ala Ser Asp Phe Glu Phe Gly Val
            195                 200                 205
Asp Pro Ser Ala Asp Pro Glu Leu Ala Leu Ala Leu Arg Val Ser Met
        210                 215                 220
Glu Glu Gln Arg His Ala Gly Gly Ala Arg Ala Arg Ala Arg Ala Ala
225                 230                 235                 240
Ser Ala Ala Glu Ala Gly Ile Ala Thr Thr Gly Thr Glu Asp Ser Asp
            245                 250                 255
Asp Ala Leu Leu Lys Met Thr Ile Ser Gln Gln Glu Phe Gly Arg Thr
            260                 265                 270
Gly Leu Pro Asp Leu Ser Ser Met Thr Glu Glu Glu Gln Ile Ala Tyr
        275                 280                 285
Ala Met Gln Met Ser Leu Gln Gly Ala Glu Phe Gly Gln Ala Glu Ser
        290                 295                 300
Ala Asp Ile Asp Ala Ser Ser Ala Met Asp Thr Ser Glu Pro Ala Lys
305                 310                 315                 320
Glu Glu Asp Asp Tyr Asp Val Met Gln Asp Pro Glu Phe Leu Gln Ser
            325                 330                 335
Val Leu Glu Asn Leu Pro Gly Val Asp Pro Asn Asn Glu Ala Ile Arg
            340                 345                 350
Asn Ala Met Gly Ser Leu Pro Pro Arg Pro Pro Arg Thr Ala Arg Arg
            355                 360                 365
Thr Arg Arg Arg Lys Thr Arg Ser Glu Thr Gly Gly Lys Gly
        370                 375                 380
```

Fig.1

SEQUENCE LISTING

```
<160> NUMBER OF SEQ ID NOS: 7

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 1

Val Cys His Ser Lys Thr Arg Ser Asn Pro Glu Asn Asn Val Gly Leu
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 2

Ile Val Cys His Ser Lys Thr Arg
1               5
```

```
<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 3

Val Cys His Ser Lys Thr Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 4

Cys His Ser Lys Thr Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 5

His Ser Lys Thr Arg
1               5

<210> SEQ ID NO 6
<211> LENGTH: 382
<212> TYPE: PRT
<213> ORGANISM: Homo sapiens

<400> SEQUENCE: 6

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys His Ser Lys Thr Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
```

115                 120                 125
Lys Arg Leu Lys Lys Glu Lys Val Asn Val Asp Ile Ile Asn Phe Gly
    130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
                180                 185                 190

Gly Gly Ala Met Leu Gly Leu Gly Ala Ser Asp Phe Glu Phe Gly Val
            195                 200                 205

Asp Pro Ser Ala Asp Pro Glu Leu Ala Leu Ala Leu Arg Val Ser Met
    210                 215                 220

Glu Glu Gln Arg His Ala Gly Gly Gly Ala Arg Arg Ala Ala Arg Ala
225                 230                 235                 240

Ser Ala Ala Glu Ala Gly Ile Ala Thr Thr Gly Thr Glu Asp Ser Asp
                245                 250                 255

Asp Ala Leu Leu Lys Met Thr Ile Ser Gln Gln Glu Phe Gly Arg Thr
                260                 265                 270

Gly Leu Pro Asp Leu Ser Ser Met Thr Glu Glu Glu Gln Ile Ala Tyr
            275                 280                 285

Ala Met Gln Met Ser Leu Gln Gly Ala Glu Phe Gly Gln Ala Glu Ser
    290                 295                 300

Ala Asp Ile Asp Ala Ser Ser Ala Met Asp Thr Ser Glu Pro Ala Lys
305                 310                 315                 320

Glu Glu Asp Asp Tyr Asp Val Met Gln Asp Pro Glu Phe Leu Gln Ser
                325                 330                 335

Val Leu Glu Asn Leu Pro Gly Val Asp Pro Asn Asn Glu Ala Ile Arg
                340                 345                 350

Asn Ala Met Gly Ser Leu Pro Pro Arg Pro Pro Arg Thr Ala Arg Arg
            355                 360                 365

Thr Arg Arg Arg Lys Thr Arg Ser Glu Thr Gly Gly Lys Gly
    370                 375                 380

<210> SEQ ID NO 7
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: This region may or may not be present
<220> FEATURE:
<221> NAME/KEY: MOD_RES
<222> LOCATION: (35)..(35)
<223> OTHER INFORMATION: May not be present
<220> FEATURE:
<221> NAME/KEY: MOD_RES
<222> LOCATION: (38)..(38)
<223> OTHER INFORMATION: His, Arg or Lys
<220> FEATURE:
<221> NAME/KEY: MOD_RES
<222> LOCATION: (39)..(39)
<223> OTHER INFORMATION: Ser or Leu
<220> FEATURE:
<221> NAME/KEY: MOD_RES
<222> LOCATION: (41)..(41)
<223> OTHER INFORMATION: Thr or Ala
<220> FEATURE:
<221> NAME/KEY: MOD_RES

```
<222> LOCATION: (43)..(163)
<223> OTHER INFORMATION: This region, or portions thereof, may or may
      not be present; see specification as filed for detailed
      description

<400> SEQUENCE: 7

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25              30

Val Asn Ile Val Cys Xaa Xaa Lys Xaa Arg Ser Asn Pro Glu Asn Asn
            35          40                  45

Val Gly Leu Ile Thr Leu Ala Asn Asp Cys Glu Val Leu Thr Thr Leu
    50              55                  60

Thr Pro Asp Thr Gly Arg Ile Leu Ser Lys Leu His Thr Val Gln Pro
65                  70              75                      80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
            115                 120                 125

Lys Arg Leu Lys Lys Glu Lys Val Asn Val Asp Ile Ile Asn Phe Gly
130                     135                 140

Glu Glu Val Asn Thr Glu Lys Leu Thr Ala Phe Val Asn Thr Leu
145                 150                 155                 160

Asn Gly Lys
```

APPROACH TO THE TREATMENT OF COMPARTMENT SYNDROME

CROSS-REFERENCE TO RELATED APPLICATION

This application is a Divisional of U.S. application Ser. No. 12/289,389, filed Oct. 27, 2008 now U.S. Pat. No. 8,309,513, which is a Continuation of International Application No. PCT/SE2007/000413, filed Apr. 27, 2007, the entire specification claims and drawings of which are incorporated herewith by reference for all purposes.

FIELD OF INVENTION

The invention relates to the field of compartment syndrome, and to various conditions associated therewith. More specifically, the invention relates to the transfer of fluid, salts and substances between cells on one hand and on the other extracellular spaces and the vascular system in a compartment, formed by a tissue, organ and/or a defined structure, in a body, optionally aimed to normalization. The closed compartment comprises structures varying in size and extent from a cell, a tissue, a defined anatomical unit to an organ in a body. The pathologically affected structure could be malfunctioning due to excessive load, trauma, toxic agents, drugs, bleeding, tumour, infection with microbes such as bacteria and/or virus, causing abnormally elevated interstitial fluid pressure, and/or in other ways diseased. The invention furthermore relates to the use of specific antisecretory proteins within the field of compartment syndrome under normal as well as pathological conditions.

BACKGROUND OF THE INVENTION

The term compartment syndrome is used in medical practice to characterize a pathological condition characterized by an abnormally increased pressure within a closed volume, a compartment, which is causing reduction or even blockage of the blood and lymph flow through a specified, defined volume. High pressure on the blood vessels impedes the blood flow through veins, capillaries and even arterioles and arteries, alters the working conditions for the interstitial fluid in the extracellular milieu, resulting in depletion of adequate supply of nutrients and oxygen for the cells and tissues within said space. An equally important factor is the lack of drainage of waste products and metabolites, often acidic, which through their accumulation further add to the impairment of the function and metabolism of the cells within said compartment. A net effect of said disturbances is that the pressure in the compartment rises and eventually approaches levels close to the systemic arterial pressure. The actual blood pressure at the entrance of the arterial vascular system to the compartment thus constitutes a key element, determining the maximal level to which the pressure may rise. In avascular structures, such as cartilage and intervertebral discs, adequate supply is dependant on transfer of fluid and other constituents to and from an area by diffusion, by cellular ion and fluid pump systems and by osmotic pressure gradients, requiring proper cell functions. If a strongly elevated CP (compartment pressure) persists, it will cause a severe injury to the involved cells, tissues and organs. Bleedings and swelling of the cells and tissues in said compartment may further add to the damage as do subsequent ischemia. The longer the elapsing time with elevated CP, the more extensive and severe the damage, which eventually turns irreversible and necrotic cell death follows. Mechanical distortion, dislocation and shearing add to the damage. Apoptotic cell death may subsequently add to the initial injury. The CS (compartment syndrome) creates alarming clinical signs such as pain, tenderness, swelling and reduction or even loss of function, and eventually necrosis. The severity of the damage is dependent on the location of the compartment, the types of cells and tissues involved, the characteristics of the extracellular milieu, the actual CP, the metabolic disturbances and its duration to mention some of the key factors of importance for the outcome and long term consequences.

Most compartments in the body are delimited by dense connective tissue, often specialized as sheaths, fasciae, tendons, ligaments, joint capsules or similar noncompliant collagenous membranes, such as the pericardium. Additionally, many endocrine organs, such as the thyroid, and exocrine glands are enclosed by and subdivided by connective tissue membranes and sheaths, therefore forming compartments. Another example of encasing, closed, rigid compartments are bone structures, such as the extremities, skull, vertebrae and facial bones. Each type of cell and tissue exposed to elevated CP is characterized by its own tolerance to prevalent metabolic and mechanical disturbances. However, relief of the CP to normal levels within reasonable time alleviates the damage.

The antisecretory protein is a 41 kDa protein that originally was described to provide protection against diarrhoeal diseases and intestinal inflammation (for a review, see Lange and Lonnroth, 2001). The antisecretory protein has been sequenced and its cDNA cloned. The antisecretory activity seems to be mainly exerted by a peptide located between the positions 35 and 50 on the antisecretory protein sequence. Immunochemical and immunohistochemical investigations have revealed that the antisecretory protein is present in and may also be synthesized by most tissues and organs in a body. Synthetic peptides, comprising the antidiarrhoeic sequence, have been characterized (WO 97/08202; WO 05/030246). Antisecretory factors have previously been disclosed to normalise pathological fluid transport and/or inflammatory reactions, such as in the intestine and the choroid plexus in the central nervous system after challenge with the cholera toxin (WO 97/08202). Addition of antisecretory factors to food and feed was therefore suggested to be useful for the treatment of oedema, diarrhoea, dehydration and inflammation in WO 97/08202. WO 98/21978 discloses the use of products having enzymatic activity for the production of a food that induces the formation of antisecretory proteins. WO 00/038535 further discloses the food products enriched in antisecretory proteins as such.

Antisecretory protein and fragments thereof have also been shown to improve the repair of nervous tissue, and the proliferation, apoptosis, differentiation, and/or migration of stem and progenitor cells and cells derived thereof in the treatment of conditions associated with loss and/or gain of cells (WO 05/030246).

There are at present no drugs available that unequivocally block the rise in pressure and turn it back to normal levels at an established CS or prevent the developing damage at a threatening or ongoing CS. Hypertonic solutions of e.g. urea or mannitol are presently used for selected patients suffering from elevated ICP (intracranial pressure), but the effects are transient lasting for just a few hours, depending on the anatomical location and the actual treatment schedule. Corticosteroids have as well been utilized to counteract elevated ICP, but serious side effects may frequently evolve. Additional drugs have been advocated, but mainly to coop arising symptoms. Lowering the body core temperature in combination with barbiturate anaesthesia is considered beneficial. There is, however, no reliable drug therapy available for CS arising in e.g. muscles, joints and nerves. Surgical intervention constitutes a frequently used treatment, but suffers from the disadvantage of per se adding extra injury and discomfort as well as risks for the development of complications.

A reliable diagnosis of an imminent, developing or established CS may be difficult to make even for an experienced physician. Diagnostic aids based on the use of e.g. ultrasound and magnetic resonance imaging (MRI) have been used, presently often in connection with computerised programs. In the present context, determination of the pressure of the interstitial fluid in the compartment to be investigated was made by measuring the actual pressure with the aid of a very small sensor at the tip of a light guiding glass fibre. The diameter of the probe was 0.4 mm and the diameter of the flexible glass fibre just 0.3 mm, meaning that the injury by the measuring equipment is not likely to be of importance, hardly adding any noticeable effect on the pressure levels. Thereby, the used equipment must be considered to present reliable values on the pressure prevailing in the compartment, both in the extracellular fluid and in certain cases also intracelluarlarly in adjacent cells and/or cell aggregates.

Antisecretory factors (AF), specifically proteins and peptides, as described in detail in WO 97/08202, are effective in abolishing hypersecretory conditions and diseases in the intestine, such as diarrhoea. Other examples related to effects of AF in relation to hypersecretory conditions are e.g. inflammatory bowel diseases, brain oedema, glaucoma, elevated intracranial pressure, Morbus Ménière, and mastitis. AF has as well been considered for the treatment of glaucoma (WO 97/08202).

SUMMARY OF THE PRESENT INVENTION

The present invention relates to the use of a pharmaceutical composition comprising an antisecretory protein, a homologue, derivative, and/or fragment thereof, having antisecretory activity, and/or a pharmaceutically active salt thereof, for the manufacture of a pharmaceutical composition and/or medical food for the treatment and/or prevention of compartment syndrome. The invention also relates to the treatment and/or prevention of various conditions associated with compartment syndrome, such as swelling of cells and tissues, infections with microbes comprising bacteria, and/or virus, and/or the formation of a tamponade, e.g. at the heart, kidney, testis, ovary, bone, joint, glands, immunolymphatic structures, nerve, brain, spinal cord, skin, muscles and/or vascular wall.

Furthermore, the invention relates to a method for the treatment and/or prevention of a compartment syndrome, such as mentioned in the above, said method comprising administering to a mammal in need thereof a therapeutically effective amount of a pharmaceutical composition and/or a medical food comprising an antisecretory protein, a derivative, homologue, and/or fragment thereof, having antisecretory activity, and/or a pharmaceutically active salt thereof. The invention is also related to various administration doses and routes suitable for the intended purpose of treatment as well as the patient's age, gender, condition etc.

The treatment according to the invention is likely to be most useful to patients at risk for developing and/or suffering from compartment syndrome, and/or from the uptake and/or release of pathogenic substances. In addition, such treatment is beneficial also in other conditions characterized by abnormal turn over of fluid and ions from enclosed compartments, such as compartments with abnormal pressures.

BRIEF DESCRIPTION OF THE DRAWINGS

FIG. 1: shows the amino acid sequence of an antisecretory protein according to SEQ ID NO:6 of the present invention. The sequence corresponds to SEQ ID NO:2 from U.S. Pat. No. 6,344,440.

FIG. 2 a demonstrates that HSV-1 infection at day 5 results in an increase in ICP in excess of 40 mm Hg. In contrast, treatment of the HSV-1 infected rat twice daily with AF, as shown in FIG. 2 b, almost turned the ICP back to normal levels. FIG. 2 c demonstrates the low ICP demonstrable in a normal, non-treated, non-infected rat. The probe was calibrated against ambient air pressure.

DEFINITIONS AND ABBREVIATIONS

Abbreviations

Figure 2A:
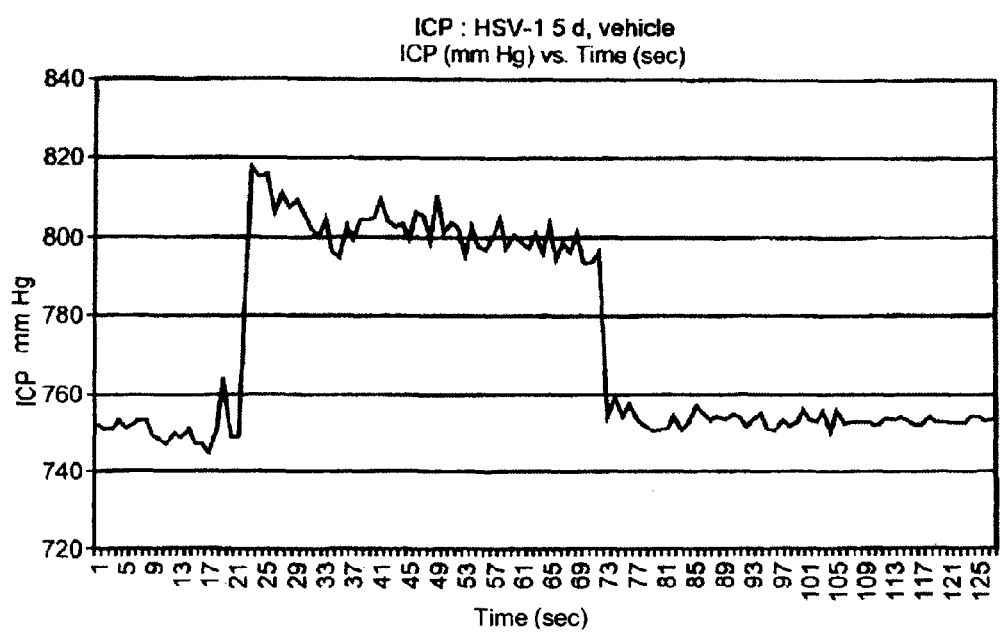
FIG. 2: ICP in rats measured with a fibre optic light guide probe implanted in the cerebral cortex in the region of the lateral ventricles.

ICP: intracranial pressure; CSF: cerebrospinal fluid; CNS: central nervous system, I.e: the brain and the spinal cord; IFP: interstitial fluid pressure; HSV: herpes simplex virus; PBS: phosphate buffered saline; CP: compartment pressure; CC: closed compartment; CS: compartment syndrome; AF: antisecretory factor, AF-16: a peptide composed of the amino acids VCHSKTRSNPENNVGL (SEQ ID NO: 1); octa peptide IVCHSKTR (SEQ ID NO: 2); septa peptide VCHSKTR (SEQ ID NO: 3); hexa peptide CHSKTR (SEQ ID NO: 4); penta peptide HSKTR (SEQ ID NO: 5).

DEFINITIONS

Herein, "compartment syndrome" is defined as an elevated pressure resulting in metabolic disturbances and eventually damage within a defined space in cells, tissues, defined structures and/or organs delimited by pressure resistant structures. The term compartment syndrome is in medical practise used to characterize a pathological condition characterized by an abnormally increased pressure within a closed volume, i.e. a compartment, which causes reduction or even blockage of e.g. the blood and/or lymph flow through a specified, defined volume. Compartment syndrome may cause as well as be caused by a variety of conditions, such as viral and microbial infections, tumours, bleedings, ischemia, trauma, excessive and/or abnormal function or load, etc, as disclosed herein. In the present context, the term "closed compartment" refers to a defined space in cells, tissues, organs and/or an anatomical structure delimited by pressure resistant structures.

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides or oligopeptides. The terms "protein" and "peptide" may be used interchangeably in the present context.

A "pharmaceutical composition", in the present context, refers to a composition comprising a therapeutically active amount of an antisecretory protein, optionally in combination with a pharmaceutically active excipient, such as a carrier or a vehicle. Said pharmaceutical composition is formulated for the appropriate route of administration, which may vary depending on the condition of the patient, as well as on other factors, such as age or preferred choice. A pharmaceutical composition comprising an antisecretory protein serves as a drug delivery system. The pharmaceutical composition upon administration presents the active substance to the body of a human or an animal. Said pharmaceutical composition may be in the form of e.g. tablets, pills, lozenges, capsules, stool pills, gels, etc, but is not limited thereto.

The term "pharmaceutically active salt", refers to a salt of an antisecretory protein, which may be any salt derived there from, based on so called Hofmeiser series. Other examples of pharmaceutically active salts comprise triflouroacetate, acetate and lysine chloride, but the invention is not limited thereto.

The term "antisecretory" refers in the present context to inhibiting or decreasing secretion, especially intestinal secretions. Hence, the term "antisecretory protein" refers to a protein capable of inhibiting or decreasing secretion in a body.

A "medical food", in the present context, refers to a food, which has been prepared with a composition with an antisecretory protein, according to the invention. Said food may be any suitable food, in fluid or solid form, such as a liquid or a powder, or any other suitable foodstuff. Examples of such matter may be found in WO 0038535.

In the present context, an "antisecretory protein", or a homologue, derivative and/or fragment thereof, may be used interchangeably with the term "antisecretory factors" or "antisecretory factor proteins" as defined in patent WO 97/08202, and refers to an antisecretory protein or a peptide or a homologue, derivative and/or fragment thereof having antisecretory activity. Hence, it is to be understood that an "antisecretory factor", "antisecretory factor protein", "antisecretory peptide", "antisecretory fragment", or an "antisecretory protein" in the present context, also can refer to a derivative, homologue and/or fragment thereof. These terms may all be used interchangeably in the context of the present invention. Furthermore, in the present context, the term "antisecretory factor" may be abbreviated "AF". Antisecretory protein in the present context also refers to a protein with antisecretory properties as previously defined in WO97/08202 and WO 00/38535. Antisecretory factors have also been disclosed e.g. in WO 05/030246. Also intended by the term antisecretory factor is egg yolk enriched in antisecretory factors as disclosed in SE 900028-2 and WO 00/38535 as further described below.

A "nebulizer", in the present context, refers to a medical device that delivers medication in the form of a mist to the airways. "Nebulizer" compressors force air through tubing into a medicine cup filled with liquid medicine. The force of the air breaks the liquid into tiny mist-like particles that can be inhaled deeply into the airways.

An "inhaler", in the present context, refers to a medical device that delivers medication in the form of dry powder to the airways. The inhaled air passes the dry powder to be inhaled and distributes the tiny particles that can be inhaled deeply into the airways. Either the subject to be treated inhales to give the required force to the air, or compressed air is used, alternatively combinations thereof.

The term "aerosol" in the present context, refers to a gaseous suspension of fine solid or liquid particles.

A "microbe", as disclosed herein, refers to a microscopic living organism, such as e.g. a bacteria, fungus, protozoa as well as virus. Other examples of microbes are given herein.

DETAILED DESCRIPTION OF THE INVENTION

The present inventors surprisingly found that the treatment of a living body with antisecretory proteins and/or peptides (AF) restores and normalizes the transfer of nutrients, waste products, metabolites, ions, water and/or other molecules at compartment syndrome (CS). Antisecretory proteins and peptides are thus surprisingly found to restore and/or normalize the transfer of water, ions, metabolites and substances that are e.g. transferred from cells, as well as from blood vessels into a closed compartment (CC). Antisecretory proteins do thereby reduce and/or contravene the damaging effects, and may as well prevent the internalization and/or the release of substances entering and/or being released from cells. The antisecretory proteins, homologues, derivatives, fragments and/or peptides thereof work irrespective of whether the initial cause of the compartment syndrome is a bleeding, trauma, heavy load, vascular disturbance, infection by microbes and/or virus, toxic agents or a combination of any of said causes. The antisecretory proteins, homologues, derivatives, fragments and/or peptides thereof thus help to improve the survival of cells and tissues in the CC. Consequently, otherwise induced damage due to the CS can be reduced, or even prevented.

There is a long felt need for improved drugs aimed for pharmacological treatment of compartment syndrome, as presently no adequate therapy is available. Beneficial effects of the antisecretory proteins according to the present invention are exemplified in the following text. The present inventors have found that antisecretory proteins, homologues, derivatives, fragments and/or peptides thereof have beneficial effects in cases of CS of different pathogenesis at a variety of different locations. Without the wish to limit the present invention to a specific scientific explanation, it is at present believed that antisecretory proteins and peptides (AF) may be able to abolish the establishment of CS in such a powerful way, and to normalize the aforementioned conditions, due to an exerted effect that antisecretory proteins and peptides (AF) are found to have on the lipid rafts and caveolae in cell membranes.

Lipid rafts are a membrane domains with an average size of 20 nanometers, characterized by focally high concentrations of cholesterol and sphingomyelin (Cf. Lodish et al., 2004; Pollard & Earnshaw, 2002; Ross & Pawlina, 2006). The lipid rafts contain a variety of integral and peripheral membrane proteins involved in mass transfer and cell signalling. Such signalling platforms float in cell membranes and are equipped with necessary elements for proper functions as receptors, coupling factors, G proteins systems, effectors, enzymes and compounds, and substrates, thereby being able to receive and convey specific ions, molecules and signals. These domains further interact with e.g. the cytoskeleton, and additionally, influence the composition and turn over of the interstitial fluid as well as its pressure. Flotillin-1 is a protein, which is an indicator of the prevalence of lipid rafts. Another marker of lipid rafts is the sphinglipid GM'. Further, lipid rafts are related to caveolae, bottle-shaped invaginations demonstrable in a large variety of mammalian cells and the sites for important cell functions such as vesicular trafficking and signal transduction as well as uptake, internalization and further intracellular processing of e.g. viruses. There is a turn over of caveolae, which additionally are related to the release and internalization of not only viruses but also microbes. There is a clustering in the cell membranes of lipid rafts and caveolae of growth factor receptors, inflammatory signal receptors, neurotransmitter receptors and systems for reuptake of neurotransmittors, ion channels, aquaporins, and other transporters. The lipid rafts and caveolae undergo rapid, dynamic changes related to the prevailing function of cells and organs at each moment.

The present inventors have recently been able to prove that antisecretory proteins, homologues, derivatives, or fragments thereof, having antisecretory and/or equivalent functional and/or analogue activity, or a pharmaceutically active salt thereof, have beneficial effects in treating and/or preventing dysfunction of lipid rafts and/or caveolae in cell membranes, such as abnormal, insufficient, hypo- and/or hyper-function.

Thus, antisecretory proteins, derivatives, homologues, and/or fragments thereof, having equivalent functional activity, and/or a pharmaceutically active salt thereof, have been shown to have a beneficial effect on dysfunction of lipid rafts and/or caveolae in cell membranes and can therefore be used to monitor and/or beneficially affect the structure, distribution and multiple functions of lipid rafts and/or caveolae in cell membranes. Examples of such beneficial affecting can be to counteract abnormal function, such as hypo- or hyper-function, to restore and/or normalize the lipid rafts or caveolae structurally and functionally, to improve survival and/or rescue at diseases, injuries, repair processes and other dysfunctions. Additionally, said antisecretory proteins can be employed for monitoring intracellular transport and release of cell products, as well as for normalizing the distribution of tissue constituents.

Examples of conditions at high risk for the threatening development of CS are trauma, either associated with bleedings or not, heavy load, tumour, or a substantial injury to an extremity, such as a leg or the chest (e.g. heart tamponade). Extreme load on a muscle or tendon may as well cause signs of a CS. The same is true at infections of an organ, a tissue or a joint. Microbial toxins, and microbes, comprising bacteria such as *Mycobacteria, Pseudomonas, Chlamydia, Cocci, Brucella,* and *Listeria,* as well as a broad spectrum of viruses may be causative agents. Excessive use of drugs and release of e.g. neurotransmitters, mucous, enzymes, and viruses are other pathogenic compounds. Tumours, primary or metastatic, as well as bleedings add to the list of examples on causes potentially resulting in a CS.

In the present context, determination of the pressure of the interstitial fluid in the compartment to be investigated is made by measuring the actual pressure with the aid of a sensor at the tip of a light guiding glass fibre. Thus, reliable values on the pressure prevailing in the compartment, and in certain cases also in adjacent cells are obtained.

It is known from the literature that e.g. many solid tumors have a high interstitial fluid pressure, hampering the transcapillary transport between the tumor cells and the blood and lymph circulation. Thereby an obstacle is created regarding the tumor treatment, due to insufficient uptake of therapeutic agents, such as cytotoxic drugs (Cf. Heldin et al., 2004). Further, the generation of free radicals will at radiation therapy be insufficient due to limitations in the ability of oxygen due to the restricted blood circulation. There is thus a great need for new treatment schedules, improving the efficacy of cancer therapy by lowering the interstitial fluid pressure.

The use of antisecretory proteins and peptides (AF) is not limited to the tissues, organs and anatomical structures described in the examples, but includes additional symptoms and diseases characterised by elevated interstitial tissue fluid pressure and by the uptake and release of specific substances.

The pharmaceutical composition according to the present invention can in one context be administrated by application topically, locally in situ, orally, in the nose, subcutaneously and/or systemically via blood vessels or via the respiratory tract.

The antisecretory factor is a class of proteins that occurs naturally in the body. The human antisecretory factor protein is a 41 kD protein, comprising 382 amino acids when isolated from the pituitary gland. The active site with regard to the compartment syndrome effect, according to the present invention, seems to be localized to the protein in a region close to the N-terminal of the protein, most likely localized to amino acids 1-163 of SEQ ID NO 6, or to a fragment of this region.

The present inventors have shown that the antisecretory factor is to some extent homologous with the protein 85a, also named Rpn 10, which constitutes a subunit of a constituent prevailing in all cells, the 26 S proteasome, more specifically in the 19 S/PA 700 cap. In the present invention, antisecretory proteins are defined as a class of homologus proteins having the same functional properties. The proteasomes have a multitude of functions related to the degradation of surplus proteins as well as short-lived unwanted, denatured, misfolded and otherwise abnormal proteins. Further, the antisecretory factor/S5a/Rpnl 0 is involved in the distribution and transportation of cell constituents, most evidently proteins.

Homologues, derivatives and fragments of antisecretory proteins and/or peptides according to the present invention all have analogous biological activity of being able to be used for the manufacture of a medicament for the treatment and/or prevention of compartment syndrome, as well as in a method for treating compartment syndrome. Homologues, derivatives and fragments, in the present context, comprise at least 4 amino acids of a naturally occurring antisecretory protein, which may be further modified by changing one or more amino acids in order to optimize the antisecretory factor's biological activity in the treatment and/or prevention of compartment syndrome.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of a antisecretory protein, peptide, homologue, derivative and/or fragment according to the invention, is also considered to be inside the scope of the present invention. In the present context the terms homology and identity are used interchangeably, i.e. an amino acid sequence having a specified degree of identity with another amino acid sequence has the same degree of homology to a specified amino acid sequence. In the present context a derivative is intended to be a protein having antisecretory activity as defined herein, being derived from another substance either directly or by modification or partial substitution, wherein one or more amino acids have been substituted by another amino acid, which amino acid can be a modified or an unnatural amino acid. For example, the antisecretory factor derivatives according to the invention may comprise an N terminal and/or a C terminal protecting group. One example of an N terminal protecting group includes acetyl. One example of a C terminal protecting group includes amide.

By proteins, homologues, derivatives, peptides and/or fragment thereof having an amino acid sequence at least, for example 95% identical to a reference amino acid sequence, it is intended that the amino acid sequence of e.g. the peptide is identical to the reference sequence, except that the amino acid sequence may include up to 5 point mutations per each 100 amino acids of the reference amino acid sequence. In other words, to obtain a polypeptide having an amino acid sequence at least 95% identical to a reference amino acid sequence, up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith Waterman) compare a subsequence in one sequence with a subsequence in a second sequence, and find the combination of sub-sequences and the alignment of those sub-sequences, which yields the highest overall similarity score. Internal gaps, if allowed, are penalized. Local algorithms work well for comparing two multidomain proteins, which have a single domain, or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

The antisecretory factor is a class of proteins that occurs naturally in the body. The human antisecretory factor protein is a 41 kD protein, comprising 382 amino acids when isolated from the pituitary gland. The active site with regard to the compartment syndrome effect, according to the present invention, seems to be localized to the protein in a region close to the N-terminal of the protein, most likely localized to amino acids 1-163 of SEQ ID NO:6, or to a fragment of this region.

In a preferred embodiment, said antisecretory protein is provided in a concentration of at least 1000 FIL units/ml in said egg yolk. In the present context one FIL unit corresponds to a 50% reduction of the fluid flow in the intestine compared to a control without supply of antisecretory factors, as disclosed in WO 00/38535 and SE 9000028-2.

In another preferred embodiment, the antisecretory proteins or a peptide or a homologue, derivative or fragment thereof having antisecretory activity according to the present invention consists of a sequence according to the following formulae (SEQ ID NO: 7):

X1-V-C-X2-X3-K-X4-R-X5 wherein X1 is I, amino acids 1-35 of SEQ ID NO 6, or is absent, X2 is H, R or K, X3 is S or L, X4 is T or A, X5 is amino acids 43-46, 43-51, 43-80 or 43-163 of SEQ ID NO 6, or is absent. The antisecretory factor according to the present invention, can be produced in vivo or in vitro, e.g. recombinantly, synthetically and/or chemically synthesized, and/or isolated from a naturally occurring source of antisecretory factors, such as from pig pituitary glands or bird's eggs. After production, the antisecretory factors may be further processed, such as by chemical or enzymatic cleavage to smaller antisecretory active fragments or by modification of amino acids. It is presently not possible to obtain antisecretory factor in pure form by purification. It is however possible to produce a biologically active antisecretory factor protein recombinantly or synthetically, as previously disclosed in WO 97/08202 and WO 05/030246. WO 97/08202 also discloses the production of biologically active fragments of this protein of 7-80 amino acids. The antisecretory factor according to the invention may further comprise an N terminal and/or a C terminal protecting group. One example of an N terminal protecting group includes acetyl. One example of a C terminal protecting group includes amide.

In a preferred embodiment of the present invention the antisecretory factor is a selected among SEQ ID NO 1-6, i.e. VCHSKTRSNPENNVGL (SEQ ID NO 1, in this context also called AF-16), IVCHSKTR (SEQ ID NO 2), VCHSKTR (SEQ ID NO 3), CHSKTR (SEQ ID NO 4), HSKTR (SEQ ID NO 5), or the amino acid sequence of an antisecretory protein according to SEQ ID NO 6 using the common one letter abbreviations for amino acids. SEQ ID NO 1, 2, and 3 have previously been disclosed in e.g. WO 05/030246. As specified in the accompanying sequence listing, some of the amino acids in the above specified sequences may be replaced by other amino acids. In the following in this paragraph, the position of a particular amino acid in a particular amino acid sequence is calculated from the left, denoting the most N-terminal amino acid as being in position 1 in that particular sequence. Any amino acid substitution(s) as specified below may be performed independently of any other amino acid substitution(s) in that sequence. In SEQ ID NO 1, the C in position 2 may be replaced by S, H in position 3 may be replaced with R or K, S in position 4 may be replaced with L, and/or T in position 6 may be replaced with A. In SEQ ID NO 2, C in position 3 may be replaced by S, H in position 4 may be replaced by R or K, S in position 5 may be replaced by L, and/or T in position 7 may be replaced by A. In SEQ ID NO 3, C in position 2 may be replaced by S, H in position 3 may be replaced by R or K, S in position 4 may be replaced by L, and/or T in position 6 may be replaced by A. In SEQ ID NO 4, C in position 1 may be replaced by S, H in position 2 may be replaced by R or K, S in position 3 may be replaced by L, and/or T in position 5 may be replaced by A. In SEQ ID NO 5, H in position 1 may be replaced by R or K, S in position 2 may be replaced by L, and/or T in position 4 may be replaced by A.

Also intended by the present invention is the combination of two or more of any of the fragments according to SEQ ID NO 1-6, optionally also in combination with egg yolk enriched in antisecretory factors.

Also intended by the present invention is the possibility of treating and/or preventing compartment syndrome by the administration of egg yolk enriched in antisecretory factors. SE 9000028-2 discloses how the formation of antisecretory factors can be stimulated in birds and antisecretory factors then being recovered or concentrated from digests of egg yolk. WO 00/38535 further discloses how such recovered or concentrated antisecretory factors can be administered to animals or humans with a food or feed, or, as more or less isolated products, formulated into pharmaceutical products. Therefore, also intended in the present application is the use of egg yolk enriched in antisecretory factors for the preparation of products, such as pharmaceutical compositions, for treating and/or preventing compartment syndrome or for use in such a method of treatment.

In one embodiment of the present invention, the pharmaceutical composition according to the invention further comprises a pharmaceutically acceptable excipient. The choice of pharmaceutically acceptable excipients and their optimum concentration for use according to the present invention can readily be determined by the skilled person by experimentation. Pharmaceutically acceptable excipients for use according to the present invention include solvents, buffering agents, preservatives, chelating agents, antioxidants, stabilizers, emulsifying agents, suspending agents and/or diluents. The pharmaceutical compositions of the invention may be formulated according to conventional pharmaceutical practice, e.g. according to "Remington: The science and practice of pharmacy", 21st edition, ISBN 0-7817-4673-6 or "Encyclopedia of pharmaceutical technology", 2nd edition, ed. Swarbrick J., ISBN: 0-8247-2152-7. A pharmaceutically acceptable excipient is a substance that is substantially harmless to the individual to which the composition is to be administered. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

The following is a review of relevant compositions for optional use in a pharmaceutical composition according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient. It should be emphasized that the invention is not limited to the use of the compositions mentioned in the following.

Parenteral Compositions:

For systemic application, the compositions according to the invention may contain conventional non-toxic pharmaceutically acceptable carriers and excipients, including microspheres and liposomes. Transcutaneous delivery constitutes alternative routes for systemic administration.

The compositions for use according to the invention may include all kinds of solid, semi-solid and fluid compositions.

The pharmaceutically acceptable excipients may include solvents, buffering agents, preservatives, chelating agents, antioxidants, stabilizers, emulsifying agents, suspending agents and/or diluents. Examples of the different agents are given below.

Example of Various Agents:

Examples of solvents include but are not limited to water, alcohols, blood, plasma, spinal fluid, ascites fluid and lymph fluid.

Examples of buffering agents include but are not limited to citric acid, acetic acid, tartaric acid, lactic acid, hydrogen phosphoric acid, bicarbonates, phosphate salts, diethylamine, etc. Examples of chelating agents include but are not limited to sodium EDTA and citric acid. Examples of antioxidants include but are not limited to butylated hydroxyl anisole (BHA), ascorbic acid and derivatives thereof, tocopherol and derivatives thereof, cysteine, and mixtures thereof.

Examples of diluents and disintegrating agents include but are not limited to lactose, saccharose, emdex, calcium phosphates, calcium carbonate, calcium sulphate, mannitol, starches and microcrystalline cellulose.

Examples of binding agents include but are not limited to saccharose, polysaccharides, sorbitol, gum acacia, sodium alginate, gelatine, starches, cellulose, chitosanes, sodium carboxymethylcellulose, methylcellulose, hydroxypropylcellulose, polyvinylpyrrolidone and polyetyleneglycol.

The pharmaceutical composition according to the invention can in one context be administrated locally or via intravenous peripheral infusion or via intramuscular or subcutaneous injection into the patient or via buccal, pulmonary, nasal, cutaneous or oral routes. Furthermore, it is also possible to administer the pharmaceutical composition through a surgically inserted shunt into a cerebral ventricle of the patient.

In one embodiment, the pharmaceutical composition used according to the present invention is formulated for intraocular, local, intranasal, oral, subcutaneous and/or systemic administration. In a preferred embodiment, the composition of the invention is administrated by application as a suspension or, even more preferably, a powder for inhalation with a spray, aerosol, inhaler or nebulizer nasally and/or to the respiratory tract.

The administration of a powder comprising antisecretory factors has the additional advantages in terms of stability and dosage. A pharmaceutical composition according to the invention can also be topically applied, intraocularly, intranasally, orally, subcutaneously and/or systemically administered via blood vessels. In a preferred embodiment, the pharmaceutical composition is formulated for intravenous, intramuscular, local, oral or nasal administration. Typically, when used for topical application to the eye, the applied concentration in the composition of the invention is from 1 µg to 10 mg per application, such as from 1 µg to 1 mg per application, preferably 50-1000 µg preferably 50-250 µg, either as a single dose per day or repeated several times per day (multiple doses), but is not limited thereto.

Systemically administrated to the blood, the dose is within the range of 0.1 µg to 10 mg per application and kg body weight, such as of 0.1 µg to 1 mg per application and kg body weight, preferably 1-1000 µg/kg body weight, such as preferably 1-50, 10-100, 100-250, or 50-500 µg/kg body weight, either as a single dose per day or repeated several times per day. When egg yolk enriched in antisecretory factors is used according to the present invention, this formulation is preferably administered orally.

Accordingly, the present invention relates to the use of an antisecretory protein or a derivative, homologue, and/or fragment thereof, having antisecretory activity, and/or a pharmaceutically active salt thereof, for the manufacture of a pharmaceutical composition and/or a medical food for the treatment and/or prevention of compartment syndrome. In one embodiment, said antisecretory protein consists of a sequence according to the following formula (SEQ ID NO: 7):

X1-V-C-X2-X3-K-X4-R-X5 wherein X1 is I, amino acids 1-35 of SEQ ID NO 6, or is absent, X2 is H, R or K, X3 is S or L, X4 is T or A, X5 is amino acids 43-46, 43-51, 43-80 or 43-163 of SEQ ID NO 6, or is absent. In another embodiment, the invention relates to the use of an antisecretory protein which comprises an amino acid sequence as shown in SEQ ID NO:1. In another embodiment, the invention relates to the use of an antisecretory protein, which comprises an amino acid sequence as shown in SEQ ID NO:2. In yet another embodiment, the invention relates to the use of an antisecretory protein, which comprises an amino acid sequence as shown in SEQ ID NO:3. In yet another embodiment, the invention relates to the use of an antisecretory protein, which comprises an amino acid sequence as shown in SEQ ID NO:4. In a yet further embodiment, the invention pertains to the use or an antisecretory protein, which comprises an amino acid sequence as shown in SEQ ID NO:5.

Furthermore, in yet another embodiment, the invention pertains to the use of an antisecretory protein which is a protein with an amino acid sequence as shown in SEQ ID NO 6, or a homologue, derivative and/or fragment thereof comprising amino acids 38-42 of SEQ ID NO 6.

In yet another embodiment, the invention relates to the use of a pharmaceutical composition as disclosed herein, which comprises two or more antisecretory proteins selected from the proteins as disclosed in SEQ ID NO:1-6, and SEQ ID NO 6 or a homologue, derivative and/or fragment thereof comprising amino acids 38-42 of SEQ ID NO 6, or a sequence as disclosed by the general formulae described herein. Said sequences are all equally preferred to be used in the present invention.

In one preferred embodiment, said antisecretory protein is provided in egg yolk enriched in such antisecretory protein, and wherein said antisecretory protein preferably is provided in a concentration of at least 1000 FIL units/ml in said egg yolk.

In one embodiment of the invention, said pharmaceutical composition further comprises a pharmaceutically acceptable excipient. Such an excipient may be any preferable excipient chosen to be appropriate for the specific purpose. Examples of excipients are disclosed herein. In another embodiment of the invention, said pharmaceutical composition is formulated for intraocular, intranasal, oral, local, subcutaneous and/or systemic administration. The chosen route of administration will vary depending on the condition of the patient to be treated and the patient's age and gender etc.

In another embodiment, the pharmaceutical composition is formulated for administration as a spray, aerosol or by a nebulizer or an inhaler. In yet another embodiment, the invention relates to a pharmaceutical composition and/or a medical food which is formulated for administration systemically to the blood at a dose of 0.1 pg to 10 mg per application and kg body weight, such as of 0.1 pg to 1 mg per application and kg body weight, preferably 1-1000 pg/kg body weight, such as preferably 1-50, 10-100, 100-250, or 50-500 pg/kg body weight, either as a single dose per day or repeated several times per day. In another embodiment, said dose is 1-100 pg per application and kg body weight and day The amount of the pharmaceutical composition which is distributed to the patient in need thereof will of course vary depending on the patient to be treated, and will be decided by the skilled person, such as a medical practitioner, for each occasion. Said administration can be performed either as a single dose or as multiple daily applications.

In one embodiment, the invention relates to the use of an antisecretory protein, a derivative, homologue, and/or fragment thereof, having antisecretory activity, and/or a pharmaceutically active salt thereof, for the manufacture of a pharmaceutical composition and/or a medical food for the treatment and/or prevention of compartment syndrome, wherein said syndrome causes abnormal swelling of cells and tissues. In another embodiment, said compartment syndrome is caused by a non-normal (abnormal) load, injury or disease related to a muscle, nerve, blood vessel and/or a tendon. Such a non-normal load on a muscle, nerve, blood vessel, joint and/or a tendon may e.g. occur at a trauma, extended motor activity, or at a high load. Further, drugs may cause elevation of interstitial tissue fluid pressures as well as cell swelling. In another preferred embodiment, said syndrome is caused by a microbe. In the context of the present invention, said microbe can be a bacterium, as well as a viral infection, e.g. either by a RNA virus or a DNA virus, such as Herpes viridae, such as Herpes Simplex Virus Type 1, Papovaviridae, Orthomyxoviridae, Flaviviridae, Togaviridae, Hepadnaviridae, Human Immunodeficiency Virus or Hepatitis C virus, which are all encompassed by the present invention. In another embodiment, the invention relates to the use of an antisecretory protein or a derivative, homologue, and/or fragment thereof, having antisecretory activity, and/or a pharmaceutically active salt thereof, for the manufacture of a pharmaceutical composition and/or a medical food for the treatment and/or prevention of a viral and/or microbial infection and or symptoms associated with a viral and/or microbial infection. Examples of a bacterial infection encompassed by the present invention, does include infections by pathogenic strains, such as *Mycobacteria, Pseudomonas, Chlamydia, Brucella* and *Listeria*. The present invention is however not limited thereto. In one embodiment of the invention, said microbe, such as a bacterium releases enzymes, toxins and/or pigments and/or induce the formation and/or release of reactive factors by adjacent cells and tissues. Furthermore, in the context of the present invention, said microbe can be selected from the group consisting of a Protista, Protozoan, worm, or a fungus.

In another embodiment, said syndrome is caused by a prion. A prion can be defined as a proteinaceous infectious particle, an infectious protein particle similar to a virus but lacking nucleic acid and is thought to be the agent responsible for scrapie and other degenerative diseases of the nervous system. A prion is a type of protein that is considered to be the cause of many nervous system disorders such as Creutzfeldt-Jakob's Disease, including sporadic, genetic and acquired variants thereof, constituting the corresponding human form of mad cow disease, scrapie and related conditions and diseases. In yet another embodiment, said syndrome is caused by abnormal transport of products in a cell or tissue.

In yet another embodiment of the invention, said syndrome causes ischemia. Ischemia can be defined as a low oxygen state, which is usually due to obstruction of the arterial blood supply or inadequate blood flow leading to hypoxia in the tissue. In yet another embodiment, said syndrome is caused by a drug and/or a therapeutic or diagnostic measure.

In another embodiment of the invention, said compartment syndrome is caused by bleedings, such as bleedings in the skull and/or in the brain and/or in the spine and spinal cord and/or from aneurysms, which is a sac formed by the dilatation of the wall of an artery, a vein or the heart. In another embodiment, said syndrome is caused by a tamponade of an organ or structure enclosed by a capsule, such as a heart, testis, ovary, glands, lymphoid organ and/or kidney. Cardiac tamponade is the compression of the heart caused by blood or fluid accumulation in the space between the myocardium (the muscle of the heart) and the pericardium (the outer covering sac of the heart). In yet another embodiment, said syndrome is caused by a benign and/or a malign and tumour present anywhere in a body and/or is related to the treatment of the tumour and/or adjacent structures. Tumours are characterized by elevated interstitial pressures, which may reduce the availability of tumour cells for drugs and therapeutic measures. Further, the elevated pressure in a tumour may affect its tendency to metastatic dissemination. Additionally, tumours may by their expansion in size cause increased pressure in adjacent normal tissues and organs, generating a CS. Thus CS is a frequent and serious complication in many victims suffering from tumours. In yet another embodiment, said syndrome is caused by an immune reaction. Furthermore, in one embodiment, said syndrome causes damage to or alternatively could be a consequence of injury or a trauma to intervertebral discs.

In a further embodiment, said syndrome is caused by a cytotoxical swelling of a joint and/or a tendon and/or a ligament. Furthermore, in another aspect of the invention, said syndrome is caused by a cytotoxically dependant swelling of a nerve and/or a blood vessel wall. In yet another embodiment, said syndrome is caused by a drug and/or a pharmaceutical composition. In yet another embodiment, said syndrome is caused by side effects caused by treatment of a tumour with x-ray, high energetic radiation, local cooling, local heating, light therapy and drugs used for the treatment of the tumour.

In another aspect, the present invention relates to a method for the treatment and/or prevention of compartment syndrome in a mammal in need thereof said method comprising administering an effective amount of a pharmaceutical composition comprising an antisecretory protein or a derivative, homologue, and/or fragment thereof having antisecretory activity, and/or a pharmaceutically active salt thereof. In one embodiment, the invention relates to a method, wherein said antisecretory protein consists of a sequence according to the following formula X1-V-C-X2-X3-K-X4-R-X5 (SEQ ID NO: 7) wherein X1 is I, amino acids 1-35 of SEQ ID NO:6, or is absent, X2 is H, R or K, X3 is S or L, X4 is T or A, X5 is amino acids 43-46, 43-51, 43-80 or 43-163 of SEQ ID NO 6, or is absent. In another embodiment, the present invention relates to a method, wherein said antisecretory protein comprises an amino acid sequence as shown in SEQ ID NO:1. In yet another embodiment, the present invention relates to a method, wherein said antisecretory protein comprises an amino acid sequence as shown in SEQ ID NO:2. In yet another embodiment, the invention relates to a method, wherein said antisecretory protein comprises an amino acid sequence as shown in SEQ ID NO:3. Furthermore, the invention relates to a method wherein said antisecretory protein comprises an amino acid sequence as shown in SEQ ID NO:4. In yet another embodiment, the present invention relates to a method wherein said antisecretory protein comprises an amino acid sequence as shown in SEQ ID NO:5. In yet another embodiment, the invention pertains to a method, wherein said antisecretory protein is a protein with an amino acid sequence as shown in SEQ ID NO:6, or a homologue, derivative and/or fragment thereof comprising amino acids 38-42 of SEQ ID NO:6. In one embodiment, the invention relates to a method, wherein said pharmaceutical composition comprises two or more antisecretory proteins selected from the proteins SEQ ID NOs:1-6, and SEQ ID NO:6 or a homologue, derivative and/or fragment thereof comprising amino acids 38-42 of SEQ ID NO:6, or a sequences as described by the general formula herein. Furthermore, in one embodiment, the invention relates to a method as disclosed herein, wherein said antisecretory protein is provided in egg yolk enriched in such antisecretory protein, and wherein said antisecretory protein preferably is provided in a concentration of at least 1000 FIL units/ml in said egg yolk. In yet another embodiment, the invention relates to a method wherein said pharmaceutical composition further comprises a pharmaceutically acceptable excipient. In one embodiment, said pharmaceutical composition is formulated for intraocular, intranasal, oral, local, subcutaneous and/or systemic administration. In yet another embodiment, said pharmaceutical composition and/or medical food is formulated for administration as a spray, aerosol, or by a nebulizer or an inhaler. Also encompassed by an embodiment of the present invention, is a method, wherein the pharmaceutical composition is formulated for administration systemically to the blood at a dose of 0.1 µg to 10 mg per application and kg body weight and day, preferably 1-1000 µg per application and kg body weight and day. In one embodiment of said method, said administration is performed either as a single dose or as multiple daily applications. The present invention also relates to a method for the treatment and/or prevention of compartment syndrome in a mammal in need thereof, said method comprising administering an effective amount of a pharmaceutical composition comprising an antisecretory protein or a derivative, homologue, and/or fragment thereof, having antisecretory activity, and/or a pharmaceutically active salt thereof, wherein said syndrome causes abnormal swelling of cells and tissues. In one embodiment, said syndrome is caused by a non-normal load, injury or disease related to a muscle, nerve, blood vessel, joint, and/or tendon. In another embodiment, said syndrome is caused by a microbe. In yet another embodiment, said syndrome is caused by a viral infection. In one embodiment, such a viral infection is caused by DNA virus or by RNA virus, such as Herpes viridae, Herpes Simplex Virus Type 1, Flaviviridae, Papovaviridae, Orthomyxoviridae, Hepadnaviridae, Togaviridae, Hepatitis C Virus and/or Human Immunodeficiency Virus, which are all encompassed by the present invention.

In one preferred embodiment, the present invention also relates to a method for the treatment and/or prevention of compartment syndrome in a mammal in need thereof, said method comprising administering an effective amount of a pharmaceutical composition comprising an antisecretory protein or a derivative, homologue, and/or fragment thereof, having antisecretory activity, and/or a pharmaceutically active salt thereof, wherein said syndrome is caused by a microbe, such as, but not limited to Protista, Protozoan, worm, fungus, bacteria. In one embodiment, said bacterium is selected from the group consisting of *Mycobacteria, Pseudomonas, Chlamydia, Cocci, Brucella* and *Listeria*. In yet another embodiment, said microbe, such as a bacterium, releases enzymes, toxins and/or pigments, and/or induces the formation and/or release of reactive factors by adjacent cells and tissues. In another embodiment of the invention, said syndrome is caused by a prion. In yet another embodiment, said syndrome is caused by abnormal transport of products in a cell or tissue. In yet another embodiment, said syndrome causes ischemia. In yet another embodiment, said syndrome is caused by a drug and/or a therapeutic or diagnostic measure. Furthermore, the present invention also encompasses an embodiment, wherein said syndrome causes an abnormal function of the brain and spinal cord. In yet another embodiment, said syndrome is caused by bleedings in the skull and/or in the brain and/or in the spine and spinal cord and/or from aneurysms. In yet another embodiment, said syndrome is caused by a tamponade of an organ or structure enclosed by a capsule, such as a heart, such as a heart, kidney, testis, ovary, glands and/or lymphoid organ. In yet another embodiment, said syndrome is caused by a benign and/or a malignant tumour present in a body or is related to the treatment of the tumour and adjacent structures.

Furthermore, also encompassed by the present invention is an embodiment, wherein said syndrome is caused by an immunoreaction. In another embodiment said syndrome causes damage to intervertebral discs.

It is furthermore to be understood and clear that a method comprising administering an effective amount of a pharmaceutical composition to a mammal in need thereof and/or the second medical use of a pharmaceutical composition comprising an antisecretory protein or a derivative, homologue, and/or fragment thereof, having antisecretory activity, and/or a pharmaceutically active salt thereof, according to the present invention, is directed to all conditions described herein to be associated with compartment syndrome.

EXPERIMENTAL SECTION

Example 1

Figure 2B:
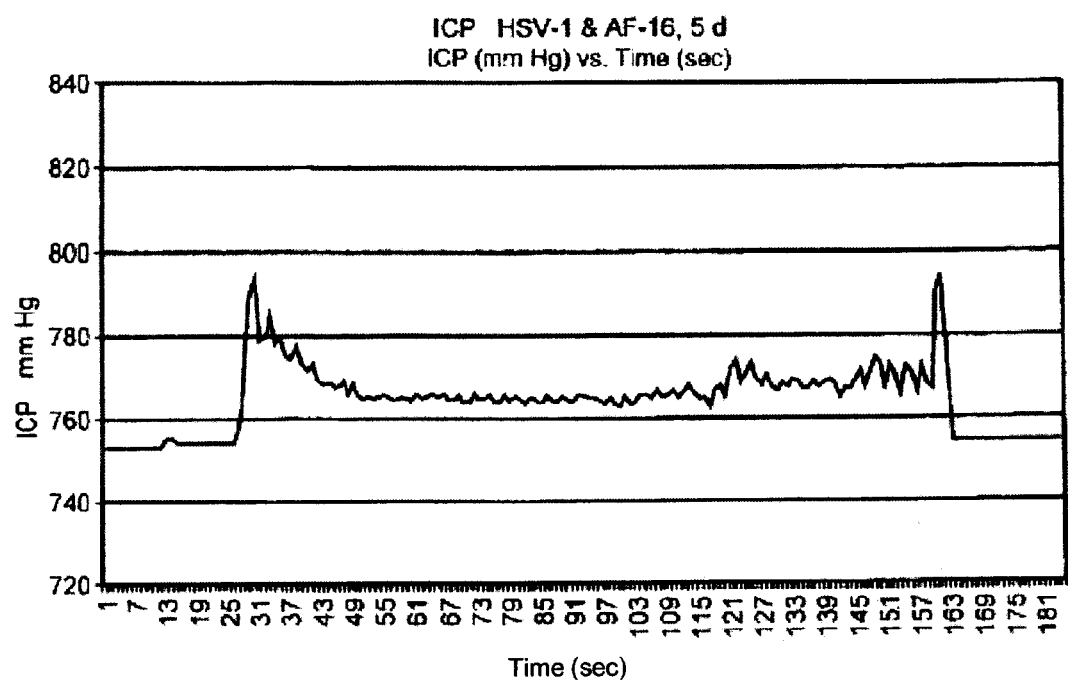
Figure 2C:
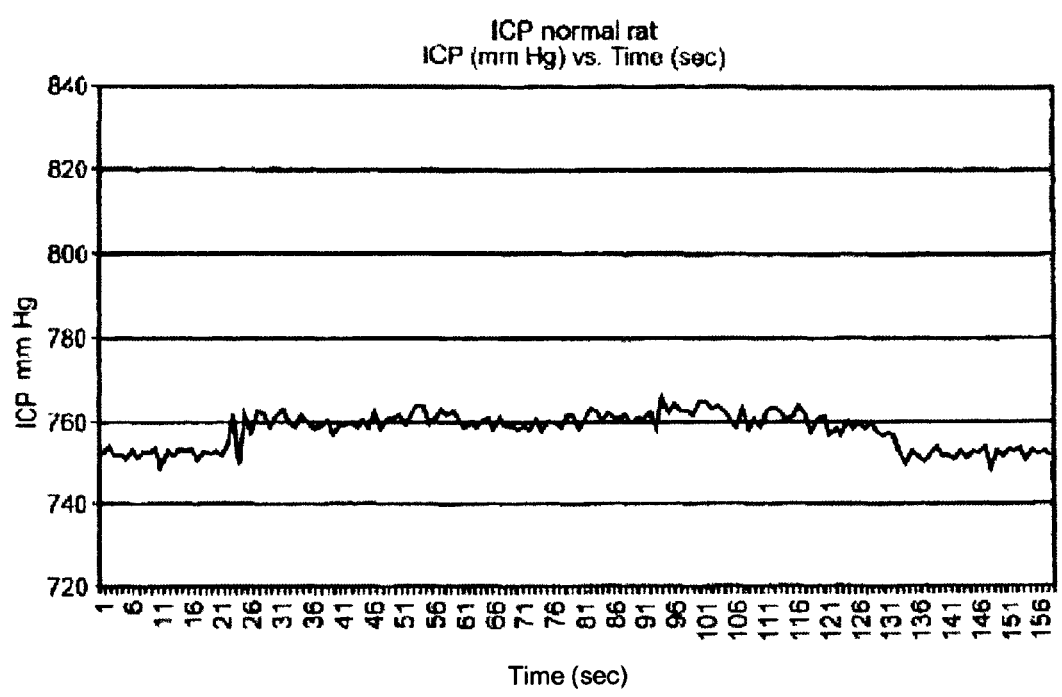

Adult rats were infected by having a solution of the Herpes Simplex virus type 1 (HSV-1; strain 2762, batch 041028; 1.7×107 PFU/mL; 25 pL) instilled in their right nostril. One group of animals (n=6) received 10 min after the infection 25 pL (10 pg) of AF-16 in their right nostril, and had thereafter the same dose of AF-16 instilled twice daily, every morning at 8 AM and every night at 6 PM, until the experiment was terminated on day 6. Additional HSV-1 infected rats (n=6) received in the nose at the same time intervals 25 pL of the vehicle, phosphate buffered saline (PBS). On day 6, the animals were anaesthetized, a surgical incision made through the skin on the head, and the skull bone freed from periostium and connective tissue. A hole with a diameter of about 1 mm was drilled through the right parietal bone and a miniature pressure sensor inserted 3-5 mm into the brain or into the lateral ventricle. A fibre optic pressure measure system (Samba System 3200 & Samba Preclin 420 sensor; Samba Sensors AB, V Frolunda, Sweden) with a very small diameter, ve. 0.4 mm, was used. Non-infected normal rats had an intracranial pressure (ICP) ranging 4-8 mm Hg, occasionally up to 12 mm Hg (FIG. 2c). HSV-1 infected rats treated with just the vehicle were measured to have as high pressures as up to 30-45 mm Hg (FIG. 2a), considerably affect the animals as reflected by symptoms of neurological dysfunction of increasing severity. In contrast, HSV-1 infected rats treated from the time of infection with AF-16 twice daily had almost normal ICP, 8-14 mm Hg (FIG. 2 b). A key observation was that intranasal treatment twice daily with AF-16 prevented the development of neurological dysfunctions such as wet nose, red eyes, hypersalivation, respiratory distress, motor instability, agitation, aggressiveness, lethargy, rapid changes in mood, repetitive movements, seizures, signs of paresis and eventually turning unconscious.

Figure 5:
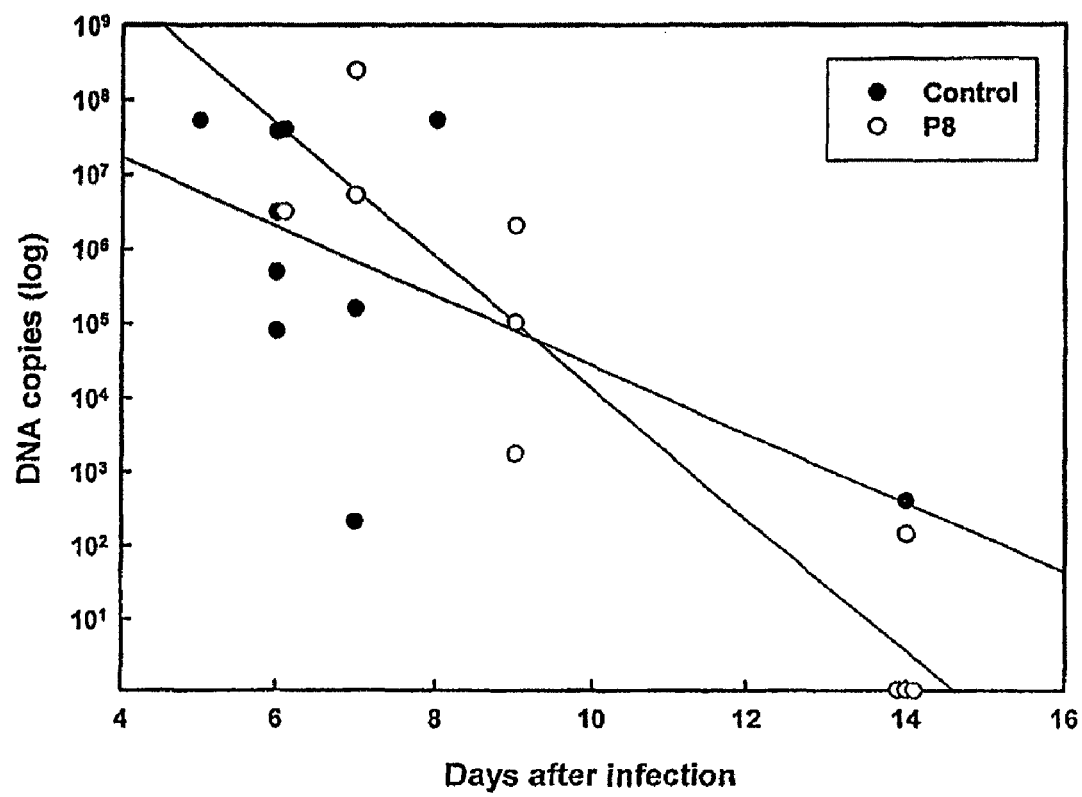
FIG. 5: Quantitative PCR performed on brain tissues from rats infected in their right nostril with HSV-1. The brain specimens were obtained between 5 to 14 days after virus inoculation in the right nostril. The results did not demonstrate any difference between the vehicle treated and the AF-treated groups as regards amount of HSV-1 DNA. Thus, AF-16 does not significantly affect the HSV-1 production in spite of the fact that the AF-16 treatment significantly improved the survival rate (FIG. 2 b), as compared to those just treated with the vehicle (FIG. 2 a).
Figure 6A:
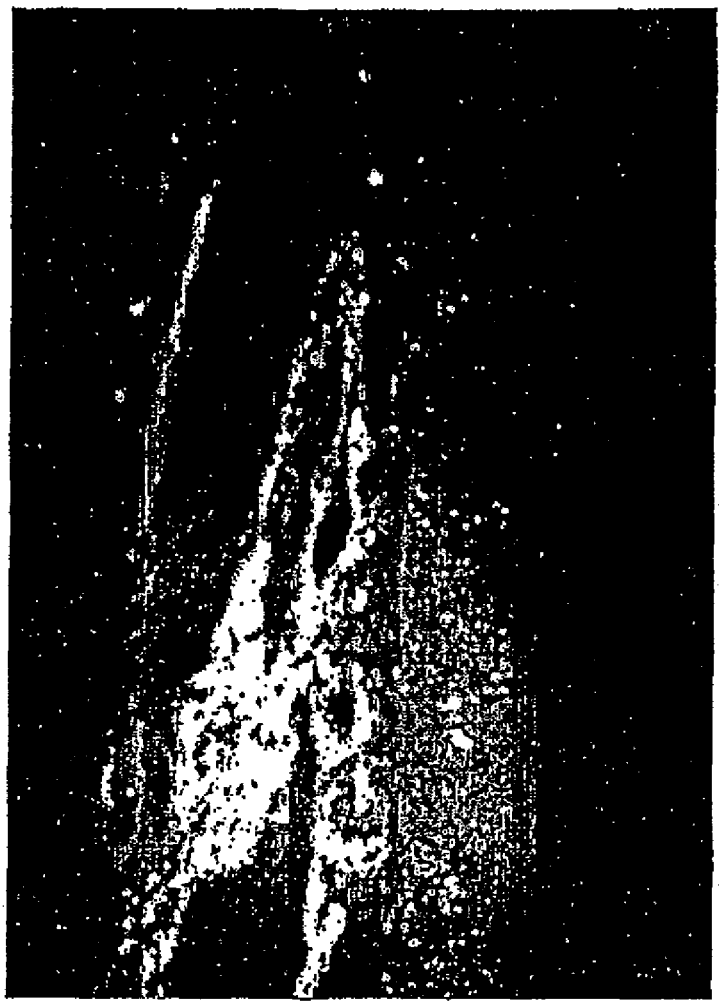
FIG. 6: Sections through the cribriform lamina, a bone structure separating the brain from the nose and through which the olfactory nerve pass. In the left figure (a) the dye-protein complex Evans blue-albumin (EBA) was infused into the subarachnoid space at day 5 after HSV-1 infection. The animal suffered from moderate encephalitis. Note that there is no red EBA in the cribriform lamina, nor in the nose, as the passage between the brain and nasal cavity is blocked. In the right figure (b) EBA was infused into the subarachnoid space of a non-infected, normal rat. Note the intense red staining throughout the cribriform plate, revealing passage of CSF from the brain (above) to the nasal cavity (below). Treatment of HSV-1 infected animals with AF-16 opened the passage for the CSF through the cribriform plate and thus resulted in a picture seemingly identical to that in a normal, non-infected animal, as outlined in Fig b.
Figure 6B:
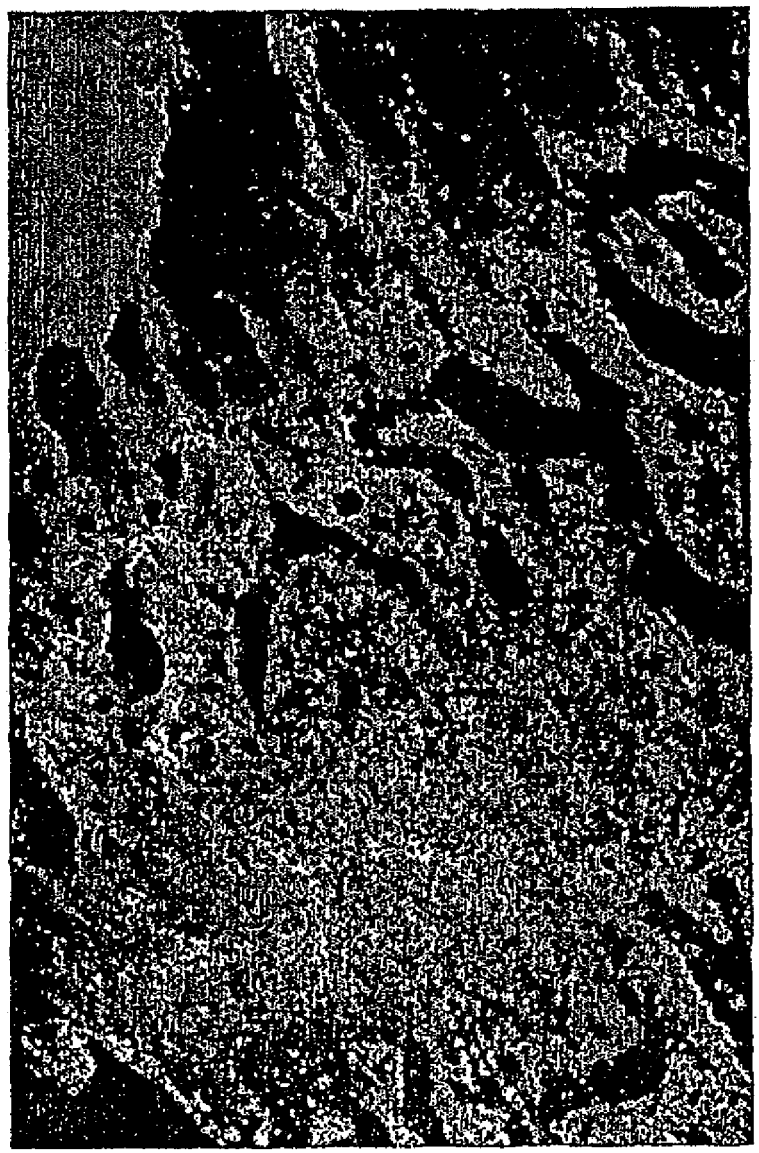

Additional HSV-1 infected animals with distinctly overt symptoms were as well treated with 10 or 25 pg AF-16 intranasally, starting on day 5, 6 or 7, i.e. after having had the vehicle during the previous days. In such cases the symptoms of neurological dysfunctions described above turned reduced within half an hour and were not demonstrable any longer after one hour. Concomitantly, the beneficial pressure reducing effects of AF-16 in such infected and AF-16 treated rats were detectable within an hour and lasted for several hours. Thus, non of the acutely AF-16 treated rats had any persistent signs of deleterious ICP and thus no CS developed. Infusion of the dye Evans blue, conjugated with bovine serum albumin (EBA), in the subarachnoid space and in the lateral ventricles resulted in normal rats that the marker after 15-30 minutes could be demonstrated in the nasal mucosa (FIG. 5 b). This demonstrates that a considerable portion of the CSF is drained to the lymphatics in the nasal mucosa and further on through cervical lymph glands, turning blue (Red if investigated by fluorescence microscopy). HSV-1 infected rats with signs of neurological dysfunctions showed if similarly having had EBA infused no staining of the cribriform lamina, neither of the nasal mucosa (FIG. 5 a). That is seen in the mentioned figure (FIG. 5 a) as there is no red staining of the right half on the figure. However, treatment with 10 or 25 pg AF-16 intranasally turned the picture in HSV-1 infected rats as in the normal, non-infected ones. Thus, intranasal infusion of AF-16 reversed the block of the outflow of CSF, induced by the HSV-1 infection. Thereby the outflow of CSF was restored and the ICP turned normal.

We conclude that treatment of rodents with AF-16 minimize the clinical symptoms on HSV-1 encephalitis and, most evidently, normalized the otherwise elevated ICP, contrasting to the deleterious effects by the very high ICP measured in those infected with HSV-1 and just treated with the vehicle, PBS. It is known from clinical practice that victims suffering from encephalitis have elevated ICP, which is of major importance as causing not only acute but as well as persisting brain damage. Actually, the high ICP is considered to be of key importance as eventually being the cause of neurological dysfunction and death. Thus, the results of our experiment #1 disclosed that the administration of AF-16 to a body suffering from a condition fulfilling the criteria for a CS did promptly counteract the pathologically elevated ICP, reduced it and even turn it to a normal level, preventing the development of neurological dysfunctions and promoting survival with no or minimal residing brain or persistent systemic malfunction.

Example 2

Figure 3:
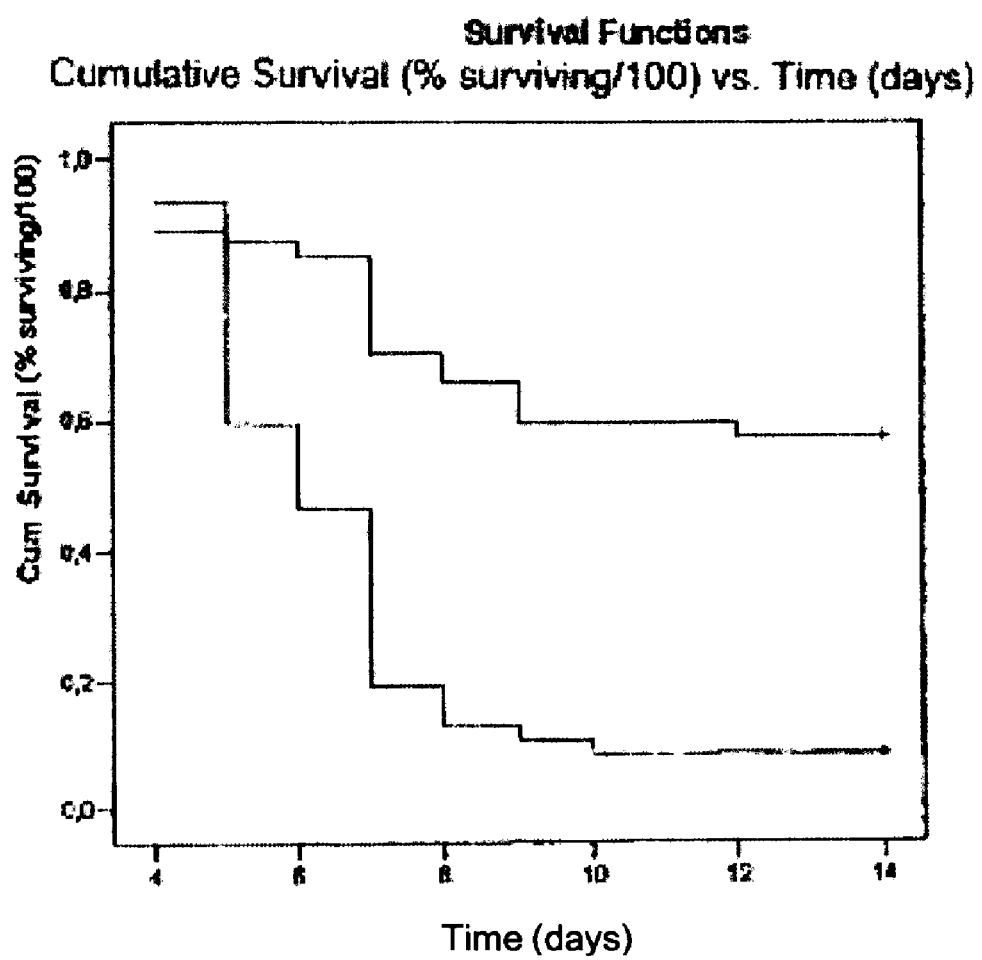
FIG. 3: Survival frequency of rats infected with HSV-1 by the administration of a virus solution in the right nostril on day 0. Half of the rats (n=15) were treated twice daily with 1 µg AF-16 (upper line), a peptide composed of the amino acids VCHSKTRSNPENNVGL (SEQ ID NO: 1), twice daily intranasally, while the other half received just the vehicle after the HSV-1 infection (lower line). Of those treated with just the vehicle only 10% survived day 14, contrasting to the 60% of those treated with AF-16. Thus, AF-16 significantly increased the survival rate at HSV encephalitis.
Figure 4A:
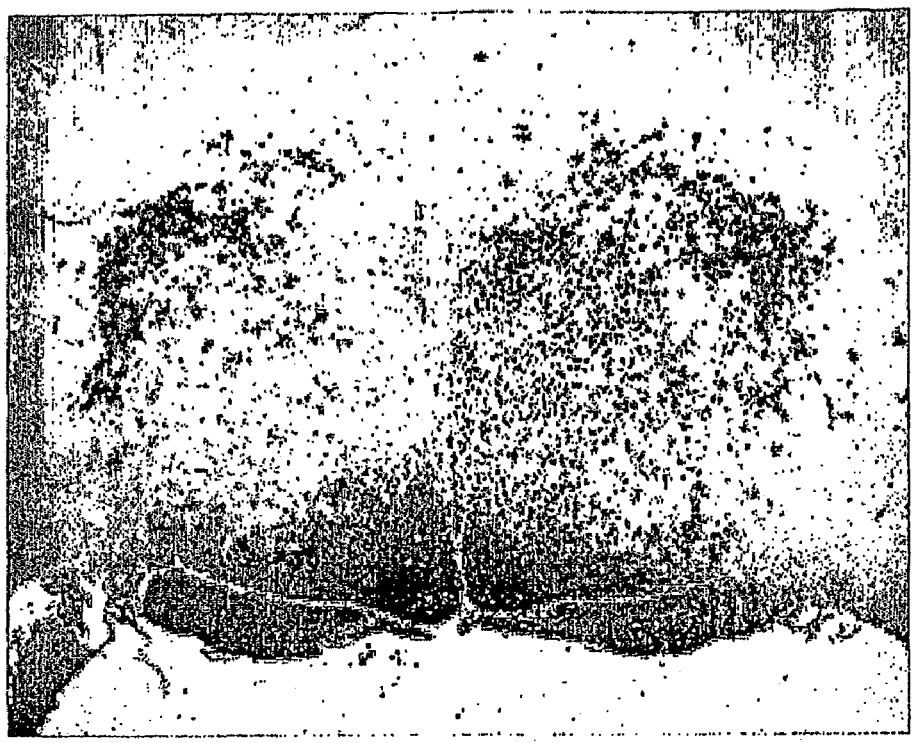
FIG. 4: Low (a, b) and high (c, d) magnifications of brain sections after HSV infection in rodents by instillation of a virus solution in the right nostril. Nerve cells with HSV protein in their cytoplasm are distinctly stained dark. Glial cells (d) in the thalamus are distinctly outlined due to their abundance of HSV proteins in their cytoplasm. Note that many of the nerve cells are non-reactive (unstained). There was no difference in frequency or distribution of HSV-1 positive brain cells between those animals that were treated with AF-16 or just the vehicle.
Figure 4B:
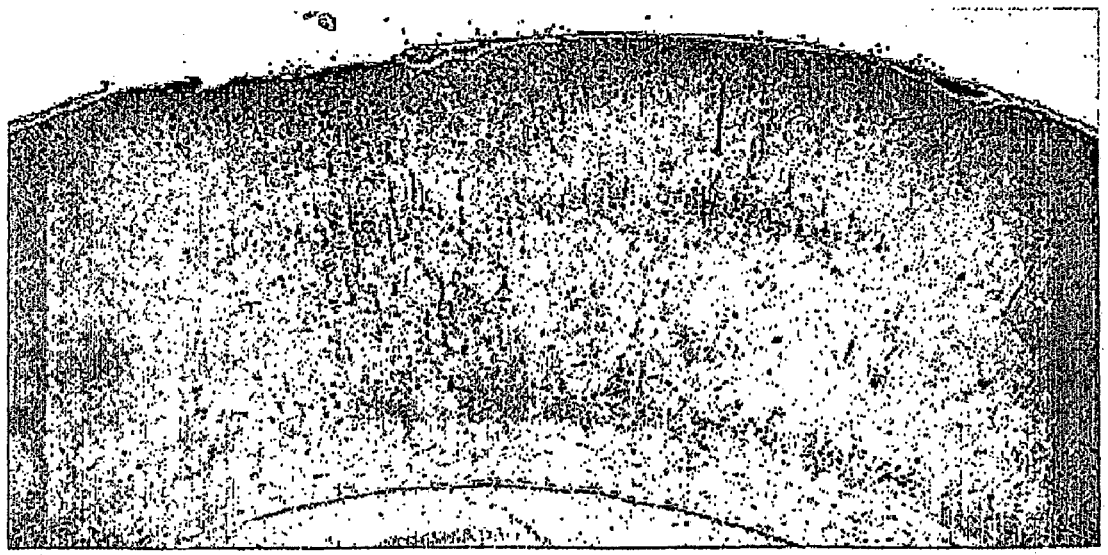
Figure 4C:
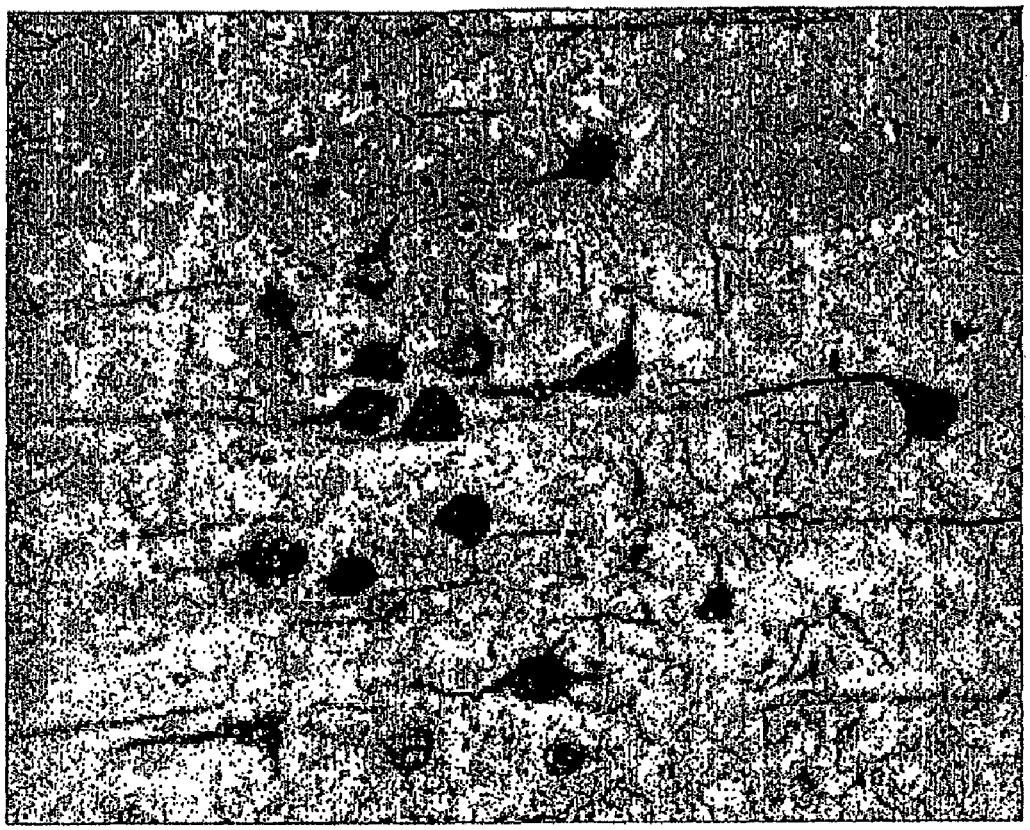
Figure 4D:
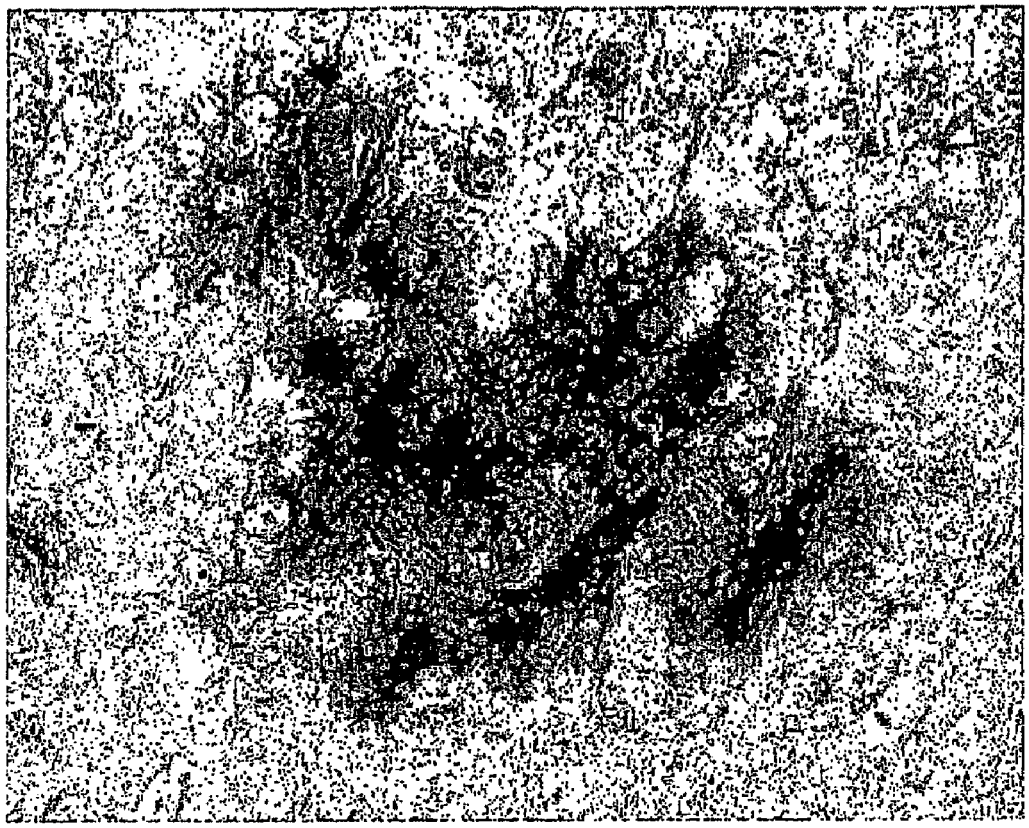

In a second experiment we investigated whether the AF-16, at a dose that reduced the elevated ICP, as disclosed in example #1, also improved the survival of adult rodents infected with HSV-1. Therefore, rats were infected by instillation in their right nostril of 25 μL of a solution of the herpes simplex virus type 1 (HSV-1; strain 2762, batch 041028; 1.7×107 PFU/mL). Half of the animals received 10 min later 25 μL (1, 10 or 25 pg) of AF-16 in their right nostril, and had thereafter the same dose of AF-16 instilled every morning at 8 AM and every night at 6 PM until the experiment was terminated on day 14. The other half of the group of HSV-1 infected rats received 25 μL of the vehicle, PBS, at the same time schedule. The animals were several times daily closely watched for signs of behavioral dysfunction or general sickness. If so, the animals were sacrificed. The FIG. 3 is illustrating the survival rates for the animals, all being infected with HSV-1. The rats treated with 1 pg AF-16 (n=15; upper line), survived to a significantly higher extent, about 60%, at the end of the 2 weeks the experiment was going on (FIG. 3). In contrast, the HSV-1 infected rats, receiving just the vehicle (n=15), died to a large extent and only 10% were still surviving at the end of the test period, day 14 (FIG. 3). All of the vehicle treated, infected rats developed signs of neurological dysfunctions. Treatment twice daily intranasally with 10 pg or with 25 pg AF-16 resulted in that all the infected animals survived, and none showed any signs of neurological dysfunction. Light microscopy of specimens, fixed in formalin and the processed according to routine procedures for histopathological and immunohistochemical investigations (Cf. Zhu, Wang & Hansson 2003), revealed inflammatory, degenerative and reactive alterations in the hippocampus, the cerebellum and the brain stem, most evidently in those infected and then treated with the vehicle. It ought to be stressed that the extent and severity of the damage were depending on the duration of the exposure and to the level of elevated ICP as well as to the survival time.

Immunohistochemical investigation of brains from infected, vehicle treated rats disclosed that e.g. the flotillin-1 and aquaporin 1 immunoreactivities in the choroid plexus were hardly demonstrable any longer. In contrast distinct flotillin-1 and aquaporin 1 immunoreactivities were readily demonstrable in the choroid plexus in infected animals treated with AF-16, similarly as in normal, non-infected, non-treated rat brains. Thus, treatment with AF-16 hampered the cell loss and facilitated the normalization of the occurrence and distribution of ordered structures such as vessels, neurons including synapses and supporting cells in the nervous system. Further, the immunohistochemically demonstrable loss of flotillin-1 and aquaporin 1 immunoreactivities in the choroid plexus strongly indicate severe disturbance of the prevalence, distribution and organization of lipid rafts, as disclosed by the loss of flotillin-1 staining, and disturbed water distribution between compartments, e.g. CSF production, turn over and flow, as revealed by the low aquaporin 1 immunoreactivity. It is concluded that AF-16 treatment of animals with HSV-1 encephalitis normalize essential functions in the central nervous system, thereby abolishing the development of elevated ICP, resulting in a CS.

It is concluded that treatment by instilling 1, 10 or 25 pg AF-16 twice daily in a nostril significantly increased the survival rate of adult rats infected with encephalolitogenic HSV-1 and abolished the development of neurological dysfunctions. Such effects are likely due to that the treatment with AF-16 prevented the ICP to increase to damaging levels, as demonstrated in example #1, in the CC formed by the skull, and turned the ICP to about normal values, preventing the development of a injurious CS.

Example 3

An alternative explanation to the improved survival of HSV-1 infected animals could be that the treatment with AF-16 prevented the virus from multiplying and/or spreading in the brain. This was demonstrated not to be the case by the following experiment. Adult rats were infected by having a solution of the herpes simplex virus type 1 (HSV-1; strain 2762, batch 041028; 1.7×107 PFU/mL) instilled in their right nostril. Half of the animals received 10 min later 25 pi_ (1 or 10 pg) of AF-16 in their right nostril, and had thereafter the same dose of AF-16 instilled every morning at 8 AM and every night at 6 PM until the experiment was terminated on day 6. The other groups of the HSV-1 infected rats received at the same time intervals 25 pL of the vehicle, PBS. The animals were closely watched for signs of general sickness and of behavioral and motor dysfunction. The animals were sacrificed by an overdose of anesthetics on day 6, the skull opened and the brain removed. The brains, including the olfactory bulbs, were fixed by immersion in buffered formalin for at least a day. The brains were the dissected and divided in several specimens, which were processed for light microscopic investigation after paraffin embedding and sectioning. The sections were processed for routine staining and for immunohistochemical visualization of HSV-1 proteins (FIG. 4). A striking finding was that HSV-1 proteins could be demonstrated in not only nerve cells (FIG. 4a-c) but also in glial cells (FIG. 4d) in the brain, including in the olfactory lobe and in the trigeminal ganglia. Note the distinct staining of the nerve cells (black in FIG. 4a-c). There was, however, no obvious difference with regard to the prevalence and distribution of HSV-1 proteins in the brains from the infected animals treated with AF-16 as compared to those treated with only the vehicle. In parallel, mice were infected with HSV-1 and the either treated with AF-16 or the vehicle by instillation twice daily in the right nostril and after six days sacrificed and brain specimens processed as above for the demonstration of HSV antigens, as described. As for the rats there was no obvious difference in the distribution or extent of virus antigens related to the treatment.

We therefore conclude that the treatment with AF-16 of rodents infected with an encephalolitogenic HSV-1 strain, originally isolated from a human fatal case, does neither alter the prevalence, nor the cellular distribution of HSV-1 viral proteins in the brain, as compared to those treated with only the vehicle. Thus, treatment with AF-16 does not alter the HSV-1 distribution in the CNS. The likely cause of the significantly improved survival of rodents, as illustrated in example #2, is therefore, that the ICP was prevented from rising to damaging levels by the AF-16 in the CC formed by the skull bone, as reported in example #1. Thereby, the development of a damaging CS was abolished.

Example 4

The improved survival of the HSV-1 infected rodents, as illustrated in example #2, could tentatively be due to that AF-16 blocked or at least reduced the proliferation of HSV1 virus in the infected brain. Therefore, adult rats were infected by having a solution of the herpes simplex virus type 1 (HSV-1; strain 2762, batch 041028; 1.7×107 PFU/mL) instilled in their right nostril. Half of the infected animals received 10 min later 25 pL (1 or 10 pg) of AF-16 in their right nostril, and had thereafter the same dose of AF-16 instilled every morning at 8 AM and every night at 6 PM until the experiment was terminated on day 6. The other groups of the HSV-1 infected rats received at the same time intervals 25 μL of the vehicle, PBS. The animals were closely watched for signs of general sickness and of behavioral and motor dysfunction. The animals were sacrificed by an overdose of anesthetics on day 6, the skull was then rapidly opened and the brain removed. Thereafter, samples of brain tissue were processed by RT-PCR for evaluation of the number of HSV-1 copies demonstrable in the brain tissue, according to the routine procedures used at the Clinical Virology Laboratory, Sahlgrenska University Hospital, Goteborg, Sweden. A striking finding was that there was no significant difference with regard to prevalence and distribution of HSV-1 DNA copies in the AF-16 treated rodents as compared to those having received just the vehicle (FIG. 5). The experiment described above was also performed in mice in parallel, and similar results achieved, confirming the efficacy of AF-16 in multiple species. Thus, the AF-16 did not have any significant effects on the multiplication of HSV-1 virus, as demonstrated by the PCR data (FIG. 5). The beneficial effects are likely to be due to that AF-16 abolished the abnormal rise in ICP (FIG. 2) in the CC formed by the skull, as disclosed in example #1, which if untreated should resulted in a deleterious CS, severely damaging the CNS of the infected animals.

Example 5

The beneficial effects of AF-16 on animals suffering from HSV-1 encephalitis could tentatively be due to that AF's reduced the inflammatory reactions in the CNS. To test that hypothesis, adult rats were infected by having a solution of the herpes simplex virus type 1 (HSV-1; strain 2762, batch 041028; $1.7 \times 10^7$ PFU/mL) instilled in their right nostril. Half of the animals received 10 min later 25 µL (1 or 10 pg) of AF-16 in their right nostril, and had thereafter the same dose of AF-16 instilled every morning at 8 AM and every night at 6 PM until the experiment was terminated on day 6. The other half of the HSV-1 infected rats received at the same time intervals 25 µL of the vehicle, phosphate buffered saline. On day 6, cerebrospinal fluid (CSF) samples were taken from the animals, either treated with AF-16 (n=3), or the vehicle (n=3), according to the procedure described by Huang, Saljo and Hansson (1996). When analyzed for the concentrations of the inflammation markers IL-1, IL-6, and TNF-a, it was found that there was no significant difference in the concentrations of either in the CSF from the infected animals treated with AF-16 as compared to those having been treated with the vehicle. It is concluded that treatment with AF-16 is not likely to improve the survival of rodents suffering from HSV-1 encephalitis by altering the inflammatory response, but by normalizing the intracranial pressure, thereby preventing prevalence of high ICP in a CC and thereby the development of a CS. The deleterious effects caused by the HSV-1 encephalitis were thus considered to be due to that AF hampered the development of a CS.

Example 6

A different type of cerebral CS was induced by the injection of antilogous whole blood in the subarachnoid space, a procedure known from the literature to result in the development of brain oedema and elevated ICP. Anaesthetized adult rats had 50-350 pL heparinzed autologous blood deposited in the subarachnoid space through a small hole drilled in the occipital bone or by injection into the cistern magna through the atlanto-occipital membrane. Holes drilled in a skull bone were eventually plugged with SuperBond@ glue. Such treatments with subarachnoidally deposited blood increased the ICP, inducing the development of a CS in a day or within a week, the exact time depending on the conditions and amount of blood deposited, in agreement with reports in the medical literature. In our experiments, injection of 0.2-0.3 mL autologous, heparinized blood in the cisterna magna in adult Sprague-Dawley rats resulted within 1-3 days in an elevation of the ICP to 13 to 30 mm Hg, as assessed with an implanted miniature pressure light guided probe (Samba System 3200 & Samba Preclin 420 sensor; Samba Sensors AB, Gruvgatan 6, SE 42130 V. Frolunda, Sweden). The ICP in normal adult rats, either non-treated or having had phosphate buffered saline (PBS) injected instead, was 6-9 mm Hg. Treatment with 25 pg AF-16 intranasally twice daily resulted in a reduction of the elevated ICP, which reproducibly turned to almost normal levels in 1-2 h. The AF treated rodents showed neither signs of impaired brain function nor any gross obvious impairment of behavioral or motor functions, in contrast to those having had blood deposited subarachnoidally and then treated with the vehicle. It is concluded that treatment with AF-16 reduced the extent and severity of the brain damage induced by subarachnoidal deposition of blood, as compared to animals just having received the vehicle, PBS. This means that AF-16 is abolishing and, in case of already established cerebral CS, reducing its severity. The prompt response to AF-16 was decisive for the beneficial effect exerted by AF-16.

Example 7

Joints are enclosed by tender, noncompliant collagen capsules, further characterised by low elasticity but plasticity. At arthritis, the pressure in the synovial fluid in the joint cavity turns elevated, and inflammation adds to the symptoms. A CS is prevalent. In order to investigate if treatment with AF-16 could prevent or at least reduce the development of such a CS, adult rats were infected by systemic injection of a solution of an arthritogenic Staphylococcus areus (SA; strain LS1). One group of animals (n=3) were treated with AF-16 while a second group of rats (n=3) just received the vehicle, PBS. After a few days the knee joints and later on additional limb and foot joints turned tender, swollen and got elevated pressure in the joint cavities, as measured with the Samba Fibre Optic Pressure probe (Samba System 3200 & Samba Preclin 420 sensor; Samba Sensors AB, Gruvgatan 6, SE 42130 V. Frolunda, Sweden), as well as in the immediately surrounding tissue. The pressure in a normal synovial large joint is 0-5 mm Hg, but could increase more than five-fold in infected, inflamed joints. The interstitial fluid pressure in the subcutaneous tissue at a distance from the infected joint was measured for comparison and found to remain within normal limits, ±2 mm Hg. In contrast, rodents with a SA infected, large joint and treated with AF-16 did not have that tender, swollen and painful joints, and close to normal pressure in the joint. Infected animals, which only received treatment with the vehicle, PBS, developed CS of with time increasing severity. Samples of the synovial fluid analyzed for prevalence of bacteria quantitatively and qualitatively from either group revealed that the number of S. areus was about the same in larger joints, irrespective of whether the rats had been treated with AF-16 or not.

We conclude that the treatment with AF-16 reduced the pressure in the infected joint after inoculation with arthritogenic microbes, e.g. bacteria, and likely also virus and immunological agents. There was, however, no difference in the multiplication or distribution in the joints of pathogenic bacteria, e.g. Staphylococcus areus (strain LS1). Therefore, the infected joints were likely to become damaged by the SA infection, as no antibiotics were administrated. The animals were, however, not allowed to survive for that long.

The major finding was that treatment with AF-16 reproducibly counteracted the otherwise elevated pressure in the affected joint, which constituted a CC. Thereby, no CS developed after treatment with AF-16 in infected joints as assessed in the present study.

Example 8

Adult rats had a CC condition induced and assessed in skeletal muscles. On the hind leg, the large vessels entering the Musculus extensor digitorum longus (EDL) were occluded for 1-3 hours by applying external pressure load (Cf. Jennische & Hansson, 1987; Jennische, Skottner & Hansson, 1987). Thereafter, the blood flow was allowed to resume, and the muscle enclosures and the skin incision repaired and sutured. This treatment resulted in an ischemic injury causing necrosis of a fraction of the EDL skeletal muscle fibers. A CS developed as the tissue and the interstitial tissue accumulated fluid in such a closed compartment and additionally the muscle tissue turned swollen and oedematous. The pressure within such an enclosed compartment increased, resulting in the development of a CS. Surgical intervention was required to prevent that parts of the skeletal muscle tissue became necrotic, if there was no additional treatment. However, if treated with AF-16, no closed compartment syndrome developed, as the reactive swelling of the injured tissue and thereby the pressure within the compartment could be demonstrated with Samba pressure sensors to turn about normal. Light microscopy of samples from the EDL muscle confirmed that treatment with AF-16 reduced the extent and volume of the tissue damage, as compared to that at vehicle treatment. Thus, treatment with AF-16 prevented the development of a CS, eventually reducing the tissue damage and loss.

Example 9

Adult rats had experimentally a CC condition induced affecting the pericardium and assessed with regard to effects of treatment with the peptide AF-16. The pericardial cavity is delimiting the heart, forming a sac filled with a minimal volume of fluid, enabling accommodation of the sliding movements resulting from the sudden and forceful contractions of the heart. The pericardial cavity is towards its periphery enclosed by a parietal membrane rich in collagen. On anaesthetized rats the pericardium was opened surgically, through a small "window" in the diaphragm and mediastinum. The inside of the pericardium was traumatized by rubbing it surgically through the incision. These animals were divided in two groups, one treated with AF-16 while the other had just the vehicle, PBS. Those, that had been treated with AF-16 for a week, had just minor accumulation of fluid in their pericardial cavity, at low pressure. In contrast, those animals that after the rubbing had been treated with the vehicle had their pericardium filled with fluid under pressure, and had further numerous fibrin strands and inflammatory cells. Additionally, the parietal pericardial envelop was swollen, inflamed and infiltrated by numerous enlarged, in parts newly formed blood vessels.

The liver, spleen, kidney and thyroid were similarly mechanically injured by compression and exposed to abrasion. AF-16 treatment could as well in those cases be demonstrated to reduce the oedema and swelling of these structures, respectively, as compared to that achieved at vehicle treatment. Further the prevalence of ascites and related types of excessive extracellular fluid at elevated pressure was reduced. Thus AF-16 reduced the extent and severity of the CS in parenchymatous organs and tissues.
The CC disaster, severely disturbing heart functions, was thus less prone to develop in the AF treated animals. Thus, AF-16 hampered the development of a cardiac CS. The same beneficial effects by AF were true for the other investigated parenchymal structures and organs.

Example 10

The intervertebral discs, which separate the vertebral bodies in the spine, adjust their dimensions according to the actual load many times a day. The water content in the avascular nucleus pulposus and the annulus fibrosus in a disc is dependant on the supply of fluid, ions, nutrients and oxygen from adjacent ligaments and from the end plates of the vertebrae (Cf. Holm et al., 2007). Vast products from an avascular disc must pass through the same obstacles prior to reaching vascular systems. Therefore, rodents, rabbits and pigs have been assessed regarding effects of AF protein and of AF peptides with regard to effects on the intervertebral discs when loaded and unloaded. It could be demonstrated that treatment with AF-16 reduced the swelling and the inflammatory reactions of injured intervertebral discs. Further, when examined by light microscopy stained sections prepared from such discs were demonstrated to have suffered less damage to the nucleus pulposus in animals treated with AF-16 as well as to have less prominent reactive alterations, otherwise expected to be recognized in the annulus fibrosus and the enclosing ligaments and adjacent connective tissue. Further, effects of AF and AF-16 d after supramaximal loads as well as after a trauma to intervetebral discs revealed that the stiffness of the intervertebral connections and the deformation induced was closer to normal after AF-16 treatment than recorded after vehicle treatment. It is thus disclosed that the AF compounds are beneficial in reducing the swelling and tissue damage at trauma or deformation and/or excessive load on intervertebral discs.

Example 11

Adult rats have had experimentally induced CS developed in defined structures enclosed by a tender enclosure, such as a tendon and a nerve, investigated with regard to whether AF-16 affect its fate. Peripheral and autonomic nerves are all delimited by an endoneurium, an perineurium and outermost an epineurium. Multiple nerve fascicles form a nerve (Cf. Hansson et al., 1987). Tendons and some of the ligaments in a body are delimited by a tender collagen membrane-like structure, the synovial sheath. The inner border layer of the latter connect the tendon with its synovial vagina, which enable sliding at minimal friction. The periphery of the latter structure is enclosed by a fibrous, membrane-like layer, the fibrous vagina. The enclosing paratendinium is in some locations hold in position and receiving nutrition by mesotendons and by vinculae (Cf. Hansson et al., 1980). Further, another lubricating device are bursae, closed fibrous sacs having a thin film of fluid and which prevent rubbing and heavy load against and between adjacent firm structures. Swelling and oedema due to excessive load and trauma as well as inflammation impair the structure and function of peripheral nerves, tendons and bursae. On anaesthetized rats the sciatic nerve was crushed with the aid of specially designed forceps, as previously described (Stemme et al., 1985; Hansson et al., 1987). Such a procedure resulted not only in impaired nerve function and structure but also in impaired blood and lymph circulation, and caused swelling of the sciatic nerve, the development of oedema, which included adjacent and enveloping structures, The IFP turned elevated, as assessed by the insertion of a Samba fibre optic pressure measuring probe in the affected tissue. Every second rat was treated with AF-16 at a high dose, starting at the time of the injury. Every second of identically treated rats solely received the vehicle. The pressure in the perineurium was determined to become elevated in a day in those treated with just the vehicle, in agreement with the macroscopically recognized swelling and local oedema, i.e. having developed a CS. In contrast, sciatic nerves treated with AF-16 turned out to have an intraneural pressure that mostly was slightly elevated or close to that measured in a normal nerve. Light microscopy of thin stained sections of injured sciatic nerves confirmed that AF-16 reduced the inflammation and the oedema and the tissue distortion. Similar results were achieved when treating injured tendons (Hansson H A et al., 1980) with AF-16, as compared to that observed after vehicle administration. Those having been treated with the vehicle developed signs of CS in contrast to those treated with AF and AF-16. It is concluded that AF-16 hamper the development of a CS at an injury to e.g. a nerve, tendon or bursa.

Example 12

During surgery and at a trauma arteries may be injured, causing the vascular wall to swell. These events will result in the development of elevated IFP in the vascular wall, resulting in inflammatory reactions and rebuilding (Hansson, Jennische & Skottner, 1987). The rats in one group had a pre-started Alza osmotic minipump, filled with AF-16, implanted subcutaneously, and connected to the site of injury with a thin silicone tube, which enabled delivery of the peptide AF-16 directly to the traumatized tissue. Additional animals had for comparison their pumps filled with the vehicle. The injured arteries were investigated either 3, 5, 7 or 14 days later. Blood vessels recovered from the vehicle-treated animals were tender, had increased outer diameter and were swollen. In contrast, those treated with AF-16 were recognized as less swollen and inflamed. The potency rate was higher for those treated with AF-16 as compared to the vehicle exposed ones. When stained and sectioned specimens of the femoral artery were investigated after 14 days it was obvious that those from rats treated with AF-16 showed less damage and less prominent inflammatory reactions and less extensive reactive alterations such as formation of a neointima comprising smooth muscle cells, as compared to those treated with solely the vehicle. Further, the number of macrophages, foam cells and lymphocytes was as well reduced by the AF-16 treatment. It is concluded AF-16 had beneficial effects on the healing of injured blood vessels.

Example 13

Tumours, malignant as well as benign, have been implanted subcutaneously and intramuscularly in rodents. Every second animal, having tumours with a diameter ranging from 10 mm to 15 mm, was treated with AF proteins or AF-16, systemically with the aid of subcutaneously implanted Alzet osmotic minipumps, by injections of AF-16 at or into the tumour. In another experiment, the AF-16 peptide was delivered from an implanted Alzet 2001 pump directly onto and/or into the tumour with a fine silicone tube. Additional rats had the AF-protein induced by their feed ort by having AF in egg yolk. For comparison, an equal number of rats received the same treatment but with the vehicle. The interstitial fluid pressure (IFP) in the tumour as well as at its adjacent regions was determined with the aid of a Samba glass fibre pressure sensor (diameter 0.4 mm), with and without a protecting tubing, as well as with equipment enabling determination of the interstitial fluid pressure by the "wick" technique. The IFP in the tumours in the vehicle-treated animals was significantly elevated, in excess of 12 mm Ng. The IFP in the adjacent connective tissue was ranging from 0 to 4 mm Hg, but could occasionally be negative. Tumours in the range of 10-15 mm, and treated with AF-16 as described above, got a reduction of the IFP, which turned reduced to usually 12 mm Hg or less. Further, AF-16 reduced the intensity and extent of the inflammatory reaction as assessed by light microscopy of stained thin sections, prepared from fixed and processed specimens.

In parallel experiments performed on rodents, beneficial effects could be demonstrated on the growth and spread of implanted tumours treated with egg yolk enriched in AF proteins, as compared to effects of the vehicle.

It is concluded that lowering of the IFP in tumours is likely to enable improved microcirculation, thereby turning the extracellular milieu less hypoxic and promoting improved penetration of anti-tumour drugs, which will as well be more efficiently distributed. It is concluded that the ability of AF-16 to reduce the IFP in tumours will enable improved efficacy of treatment with specific drugs. Further, radiation therapy is likely to be more efficient as the improved microcirculation after AF-16 treatment will increase the oxygen levels in the exposed tissue, thereby promoting the formation of free radicals, of key importance in hampering the growth of the tumour, eventually resulting in enhanced killing of tumour cells. Such effects of AF-16 on the IFP are considered to contribute to improved eradication of tumours, and to enable control of the dissemination in a victim.

Example 14

Effects of AF was investigated in addition in prokaryotic cells, which are enclosed by a complex cell wall, thereby enabling the development of elevated pressure due to hampered membrane functions. That was done in bacteria, which synthesize and release a wide variety of substances that may cause damage to mammalian cells and thus to a body. Examples on such products are pigments, enzymes and toxins, which are transferred through the outer bacterial membrane to the extracellular environment. Inhibition of such membrane activities would reduce or even block the transfer and/or release of such pathogenic substances. In order to investigate if the peptide AF-16 affected the transfer of bacterial products from its synthesis in the bacterium to its environment, the following experiment was performed. The bacterium *Staphylococcus areus*, which synthesize a yellow pigment, was cultured over night or, occasionally for 2 days, in the presence or absence of the peptide AF-16. After a day or two was the bacterial culture rinsed, and then concentrated by centrifugation. The yellow pigment formed by the *Staphylococcus areus* was extracted from the permeabilized, pelleted bacteria with methanol and the light absorption determined by spectrometry. The bacterial cultures grown in the presence of AF-16 had much more of the yellow pigment than did those exposed just to the vehicle, after correction of the measured values for number of bacteria. These results unequivocally demonstrated that the treatment with AF-16 abolished the transfer and release of constituents formed in the bacteria to the environment.

It is concluded that the presented experiment proves that AF-16 efficiently influences the intracellular mass transport and release of products from living bacteria.

SUMMARY AND CONCLUSIONS

Treatment with the peptide AF-16 abolished or at least reduced the development of elevated pressures in closed compartments. The treatment with AF further reduced the adverse clinical signs at exposure to excessive load, injury, ischemia, toxic agents, drugs and at infections. If treated with AF-16 the pressure in closed compartments did not rise to the expected injurious levels, as evident if the animal was treated with solely the vehicle. The pathological conditions treated were not related to any abolishment of hypersecretory conditions by the AF proteins and peptides. The described effect of the administration of AF peptides and proteins was usually apparent within an hour and lasted for several hours. The response to the administration of AF was prompt and reduced the detrimental effects of the elevated pressure in closed compartments considerably. The AF proteins and peptides thus were effective in the treatment of CS in a living body abolishing the development of a closed CS, otherwise deleterious for the function of the affected tissue and organ. A person skilled in the art understands that a normalization of pressure in a closed compartment facilitates the administration of other pharmaceutical preparations, aimed to reduce the cause of elevated pressure and its complications, as well as direct these pharmaceuticals to their target.

REFERENCES

1. Hansson H.-A., Jennische E, & Skottner A. Regenerating endothelial cells express insulin-like growth factor-I immunoreactivity after arterial injury. Cell Tissue Res., 1987; 250: 499-505, 1987.
2. Hansson H.-A., Lundborg G & Rydevik B. Restoration of superficially damaged flexor tendons in synovial environment. An experimental ultrastructural study in rabbits. Scand J Plast Reconstr Surg. 14, 109-114, 1980.
3. Hansson H.-A., Rozell B, & Skottner A. Rapid axoplasmic transport of insulin-like growth factor I in the sciatic nerve of adult rats. Cell Tissue Res. 1987; 247: 241-247, 1987.
4. Heldin C H, Rubin k, Pietras K & Ostman A. High interstitial fluid pressure—an obstacle in cancer therapy. Nature Reviews Cancer 4, 806-13, 2004.
5. Holm S, Baranto A, Kaigle Holm A, Ekstrom L, Sward L, Hansson T & Hansson H.-A. Reactive changes in the adolescent porcine spine with disc degeneration due to endplate injury. Vet Comp Orthop Traumatol 20, 12-17, 2007.
6. Jennische E & Hansson H.-A. Regenerating skeletal muscle cells express insulin-like growth factor I. Acta Physiol Scand. June; 130, 327-332, 1987
7. Jennische E, Skottner A & Hansson H.-A. Satellite cells express the trophic factor IGF-I in regenerating skeletal muscle. Acta Physiol Scand. 129, 9-15, 1987
8. Kumar V, Abbas, A K & Fausto N: Robbins and Cotran Pathologic Basis of Disease, 7th ed., W.B. Saunders Co., Philadelphia, 2005.
9. Lange S, & Lonnroth I. The antisecretory factor: synthesis, anatomical and cellular distribution, and biological action in experimental and clinical studies. Intern Rev. Cytology 210, 39-75, 2001.
10. Lodish H, Berk A, Matsudaira P, Kaiser C A, Krieger M, Scott M P, Zipursky S L & Darnell J. Molecular biology of the cell. 5th edit. WH Freeman & Co., New York, 2004.
11. Pollard T D & Earnshaw W C. Cell biology, Saunders, Philadelphia, 2002.
12. Ross M H & Pawlina W. Histology, a text and atlas. 5th edit., Lippincott Williams & Wilkins, Baltimore, 2006.
13. Stemme S, Hansson H.-A., Holmgren A, & Rozell B. Axoplasmic transport of thioredoxin and thioredoxin reductase in rat sciatic nerve. Brain Res. 1985; 359:140-146.
14. WO 051030246
15. WO 97/08202
16. WO 98/21978
17. U.S. Pat. No. 6,344,440

What is claimed is:

1. A method for the treatment and/or prevention of compartment syndrome comprising administering a composition comprising the antisecretory factor (AF) protein of SEQ ID NO:6, or a homolog thereof or a fragment thereof comprising amino acids 37-42 of SEQ ID NO:6 and having antisecretory activity, or a pharmaceutically active salt thereof to a subject with a tumor in an amount sufficient to decrease compartment pressure resulting from the presence of said tumor.

2. The method of claim 1, wherein said homolog or fragment consists of a sequence according to the following formula (SEQ ID NO:7)

X1-V-C-X2-X3-K-X4-R-X5 wherein X1 is I, amino acids 1-35 of SEQ ID NO:6, or is absent, X2 is H, R or K, X3 is S or L, X4 is T or A, and X5 is amino acids 43-46, 43-51, 43-80 or 43-163 of SEQ ID NO:6, or is absent, and/or a pharmaceutically active salt thereof.

3. The method of claim 1, wherein said homolog or fragment comprises an amino acid sequence as shown in SEQ ID NO:1, SEQ ID NO:2, SEQ ID NO:3, or SEQ ID NO:4, and/or a pharmaceutically active salt thereof.

4. The method of claim 1, wherein said tumor is a primary tumor or a metastasis.

5. The method of claim 1, wherein said compartment syndrome is present in said tumor and/or in a structure adjacent to said tumor.

6. The method of claim 1, wherein said compartment syndrome involves an elevated interstitial fluid pressure within said tumour and/or in an adjacent structure.

7. The method of claim 1, wherein said compartment syndrome is caused by a medical treatment of said tumor, such as treatment with X-ray, high energetic radiation, local cooling, local heating, light therapy and/or anti-tumour drugs.

8. The method of claim 1, wherein the treatment of said compartment syndrome improves the efficacy of cancer therapy by lowering the interstitial pressure in a patient in need thereof.

9. The method of claim 8, wherein said cancer therapy comprises treatment with an antitumor drug and/or radiation therapy.

10. The method of claim 9, wherein the treatment of said compartment syndrome improves the microcirculation within the tumor tissue, promotes penetration/distribution of an anti-tumor drug in a body, promotes formation of free radicals in a body, hampers the growth of a tumor and/or improves eradication of a tumor in a body.

11. The method of claim 8, wherein the treatment of said compartment syndrome improves the microcirculation within the tumor tissue, promotes penetration/distribution of an anti-tumor drug in a body, promotes formation of free radicals in a body, hampers the growth of a tumor and/or improves eradication of a tumor in a body.

12. The method of claim 1, wherein said antisecretory factor (AF) protein, homolog thereof, and/or fragment thereof is present in a pharmaceutical composition and/or a medical food.

13. The method of claim 12, wherein said pharmaceutical composition and/or medical food comprises two or more antisecretory factor (AF) proteins, homologs thereof, and/or fragments thereof selected from the antisecretory factor (AF) protein as shown in SEQ ID NO:6 or a homolog, and/or fragment thereof comprising amino acids 37-42 of SEQ ID NO:6, and a homolog, and/or fragment of the antisecretory factor (AF) protein comprising an amino acid sequence as shown in SEQ ID NO: 1, SEQ ID NO:2, SEQ ID NO:3, SEQ ID NO:4, SEQ ID NO:5, or SEQ ID NO:7.

14. The method of claim 13, wherein said pharmaceutical composition further comprises a pharmaceutically acceptable excipient.

15. The method of claim 14, wherein said pharmaceutical composition is formulated for administration into a body cavity, intraocularly, intranasally, orally, locally, cutaneously, subcutaneously, intramuscularly and/or systemically.

16. The method of claim 15, wherein said pharmaceutical composition is formulated for administration as a spray, aerosol, inhaler or by a nebulizer.

17. The method of claim 15, wherein the pharmaceutical composition is formulated for administration systemically to the blood at a dose of 0.1 µg to 10 mg per application and kg body weight and day, preferably 1-1000 µg per application and kg body weight and day.

18. The method of claim 17, wherein said administration is performed either as a single dose or as multiple daily applications.

19. The method of claim 1, wherein said antisecretory factor (AF) protein, homolog or fragment thereof is provided, in egg yolk enriched in such antisecretory protein.

20. A method for the treatment of and/or reduction in the development of compartment syndrome, said method comprising administering a composition comprising the antisecretory factor (AF) protein of SEQ ID NO:1, or pharmaceutically active salt thereof to a subject with a tumor in an amount sufficient to decrease compartment pressure resulting from the presence of said tumor in said subject.

* * * * *